United States Patent
Tsuchiya et al.

(10) Patent No.: US 8,652,132 B2
(45) Date of Patent: Feb. 18, 2014

(54) GRASPING TREATMENT DEVICE

(71) Applicant: Olympus Medical Systems Corp., Tokyo (JP)

(72) Inventors: Tomoyuki Tsuchiya, Fuchu (JP); Yuki Kawaguchi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/633,653

(22) Filed: Oct. 2, 2012

(65) Prior Publication Data

US 2013/0110155 A1    May 2, 2013

Related U.S. Application Data

(63) Continuation of application No. PCT/JP2012/057595, filed on Mar. 23, 2012.

(60) Provisional application No. 61/467,119, filed on Mar. 24, 2011.

(51) Int. Cl.
 *A61B 18/18*    (2006.01)

(52) U.S. Cl.
 USPC ............................... 606/41; 606/45; 606/205

(58) Field of Classification Search
 USPC ...................... 606/50–52, 205–207
 See application file for complete search history.

(56) References Cited

U.S. PATENT DOCUMENTS

| 6,669,690 B1 | 12/2003 | Okada et al. |
| 2010/0057117 A1 | 3/2010 | Yamada |
| 2010/0331873 A1 | 12/2010 | Dannaher et al. |

FOREIGN PATENT DOCUMENTS

| EP | 2 027 821 A2 | 2/2009 |
| JP | A-2009-514566 | 4/2009 |
| JP | A-2009-261911 | 11/2009 |
| JP | A-2010-051779 | 3/2010 |
| WO | WO 02/080798 A1 | 10/2002 |

OTHER PUBLICATIONS

International Search Report issued in International Application No. PCT/JP2012/057595 dated May 15, 2012 (with translation).
Extended European Search Report issued in European Application No. 12761381.8 dated Mar. 26, 2013.

*Primary Examiner* — Linda Dvorak
*Assistant Examiner* — Amanda Scott
(74) *Attorney, Agent, or Firm* — Oliff PLC

(57) ABSTRACT

A grasping treatment device includes a jaw attached to a distal portion of a sheath rotatably around a rotation axis perpendicular to a longitudinal axis, and opening/closing relative to a distal portion of the probe in open/close directions perpendicular to the longitudinal axis and perpendicular to the rotation axis, and a support member provided between the probe and the sheath, and preventing contact between the probe and the sheath. The support member includes a most-distal support member located on the most distal direction side, and the position of the most-distal support member coinciding with the rotation axis of the jaw in directions parallel to the longitudinal axis.

10 Claims, 20 Drawing Sheets

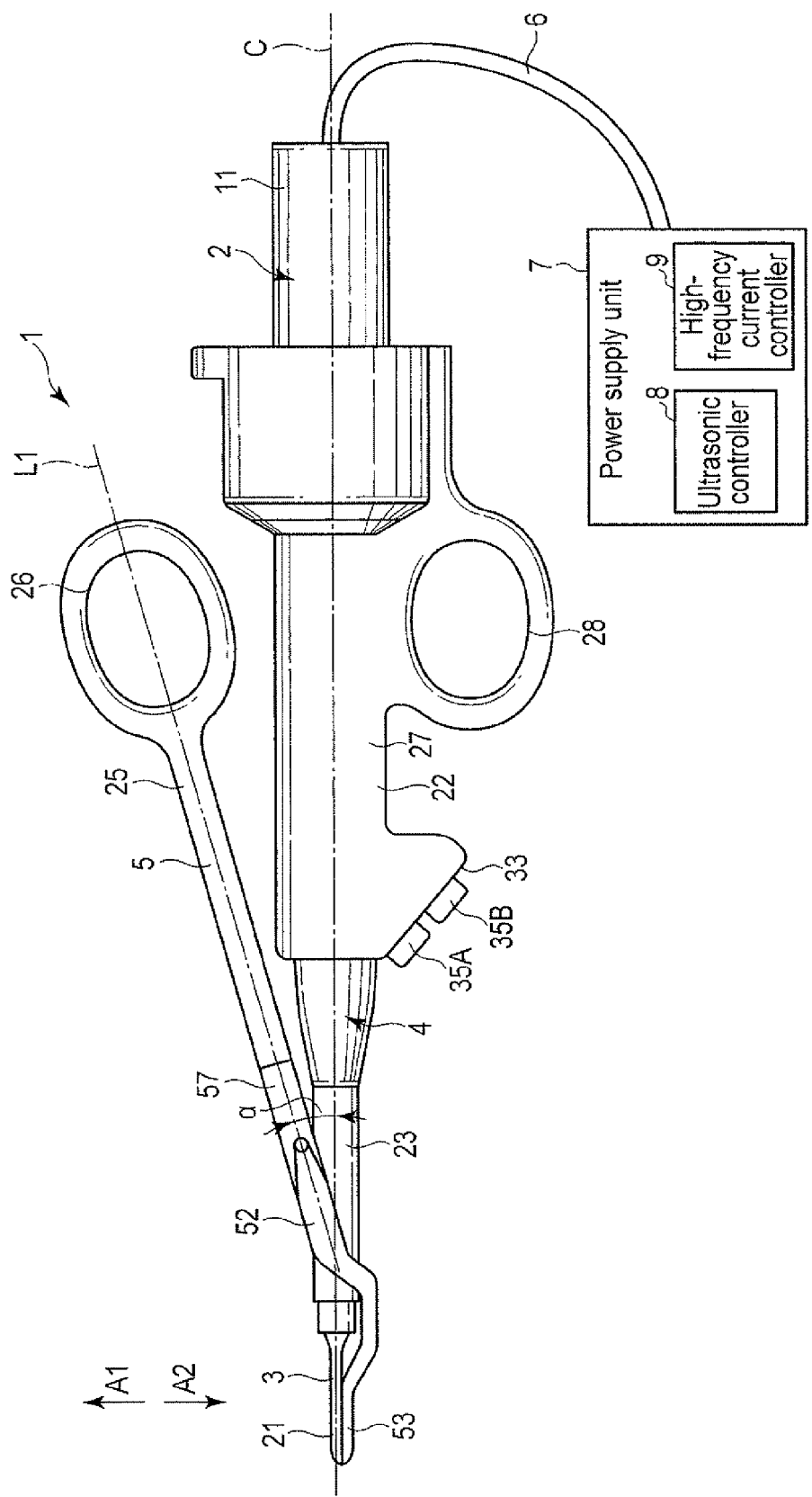
F I G. 1

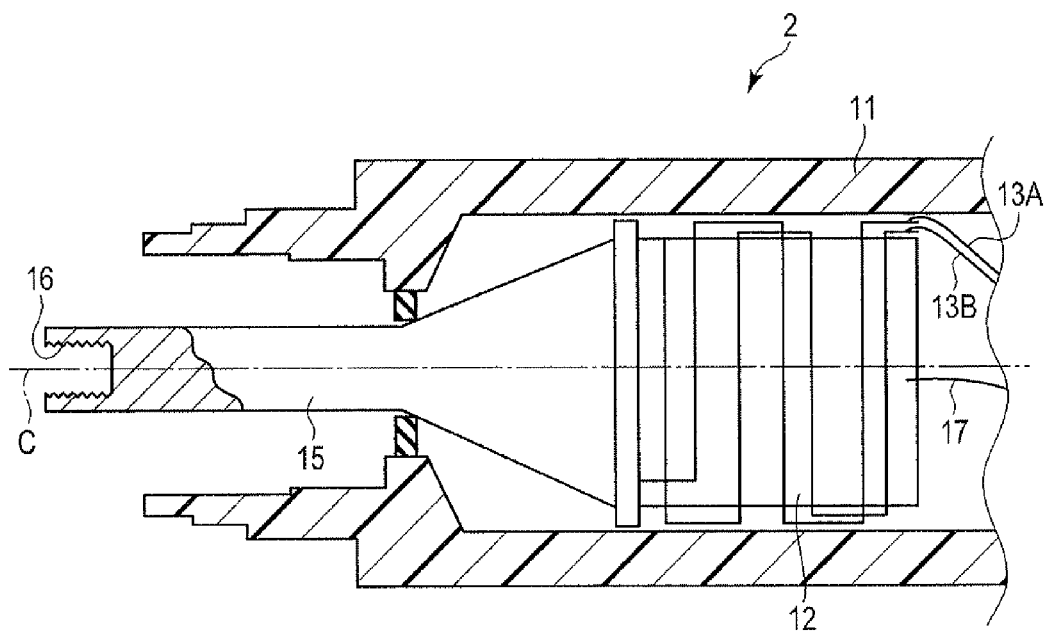
F I G. 2
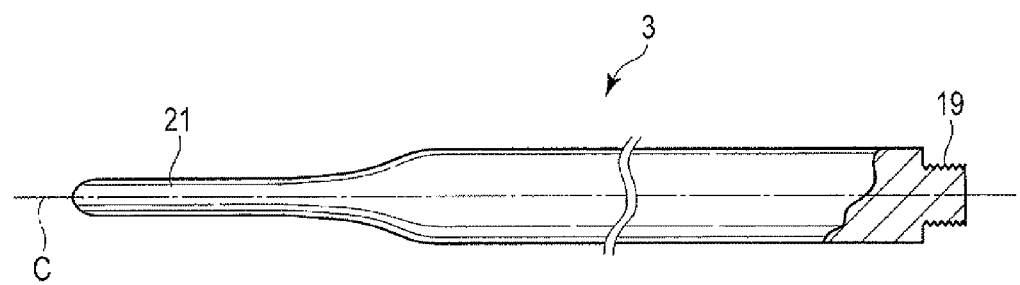
F I G. 3

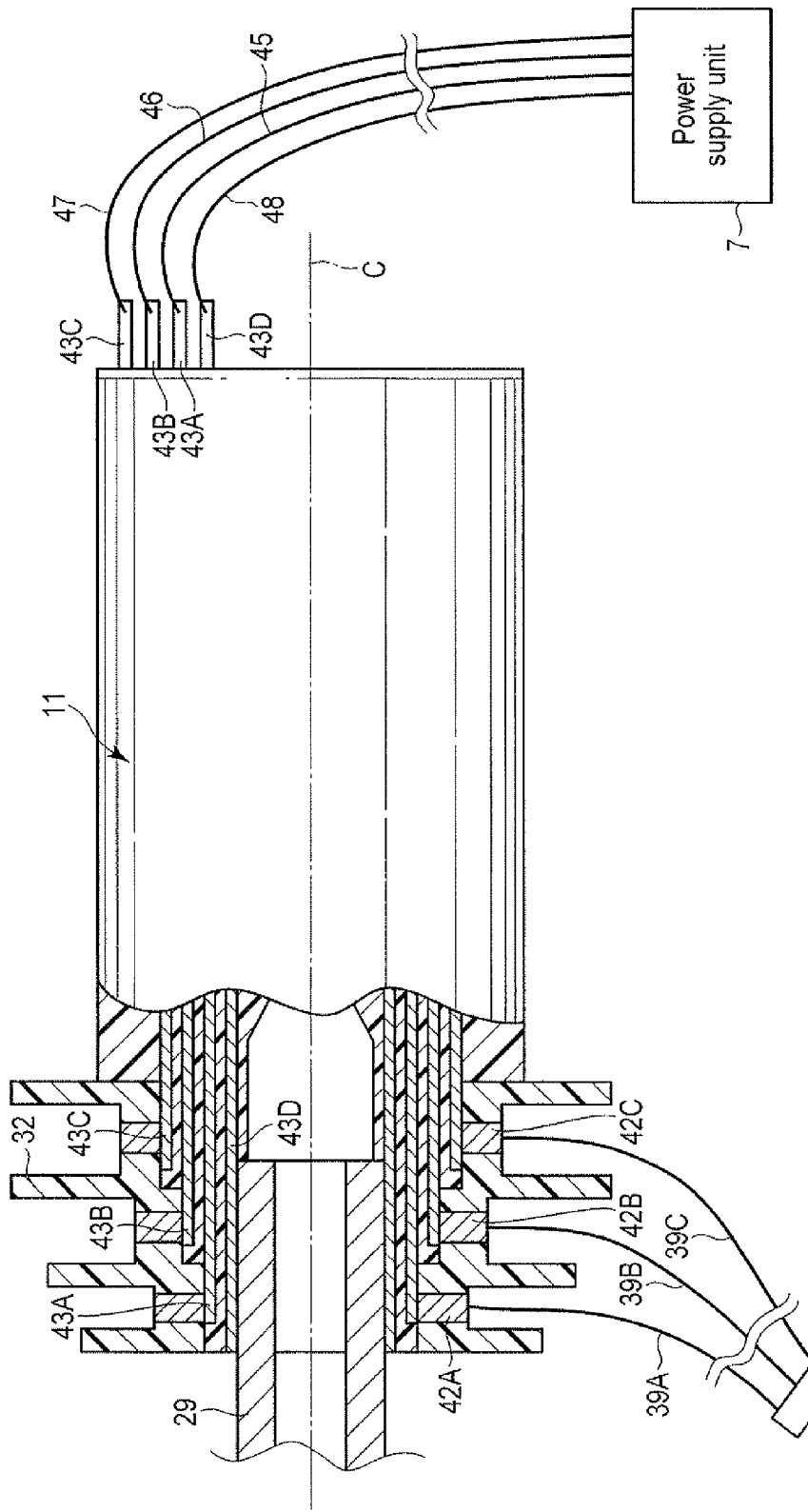
F I G. 5

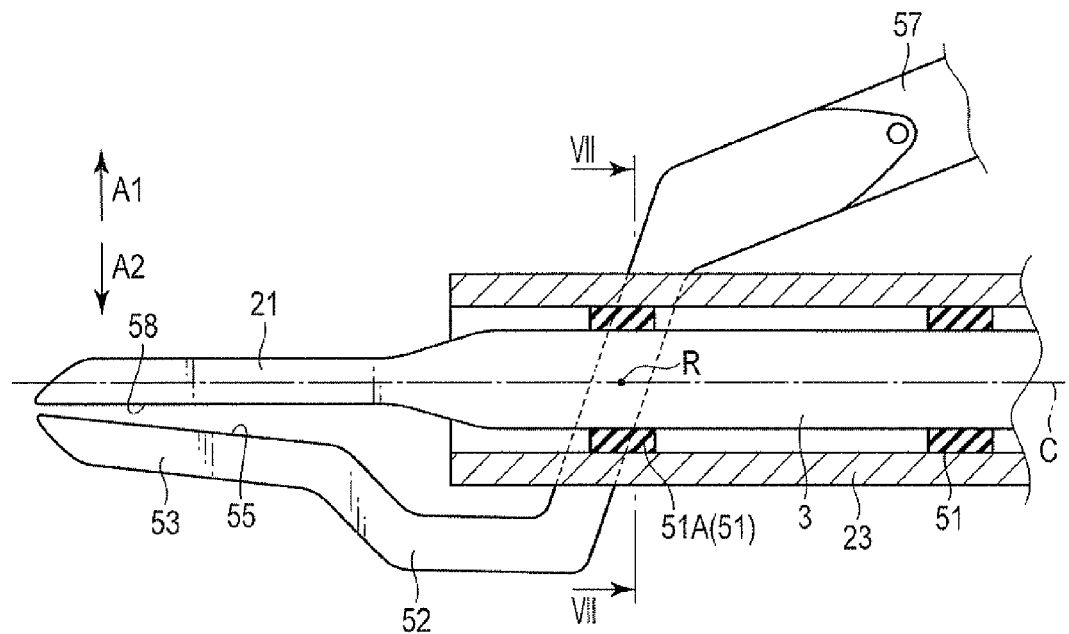
F I G. 6
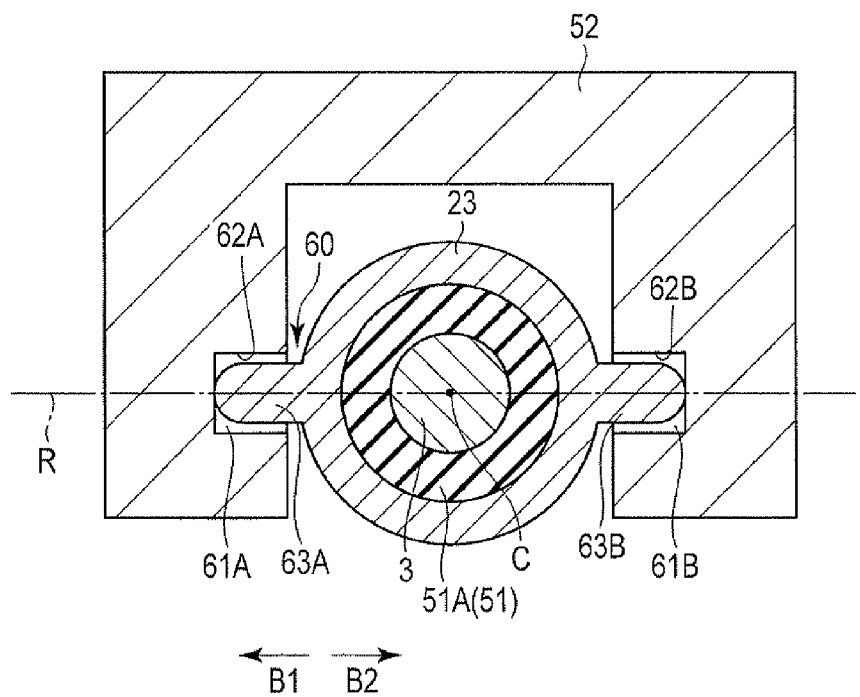
F I G. 7

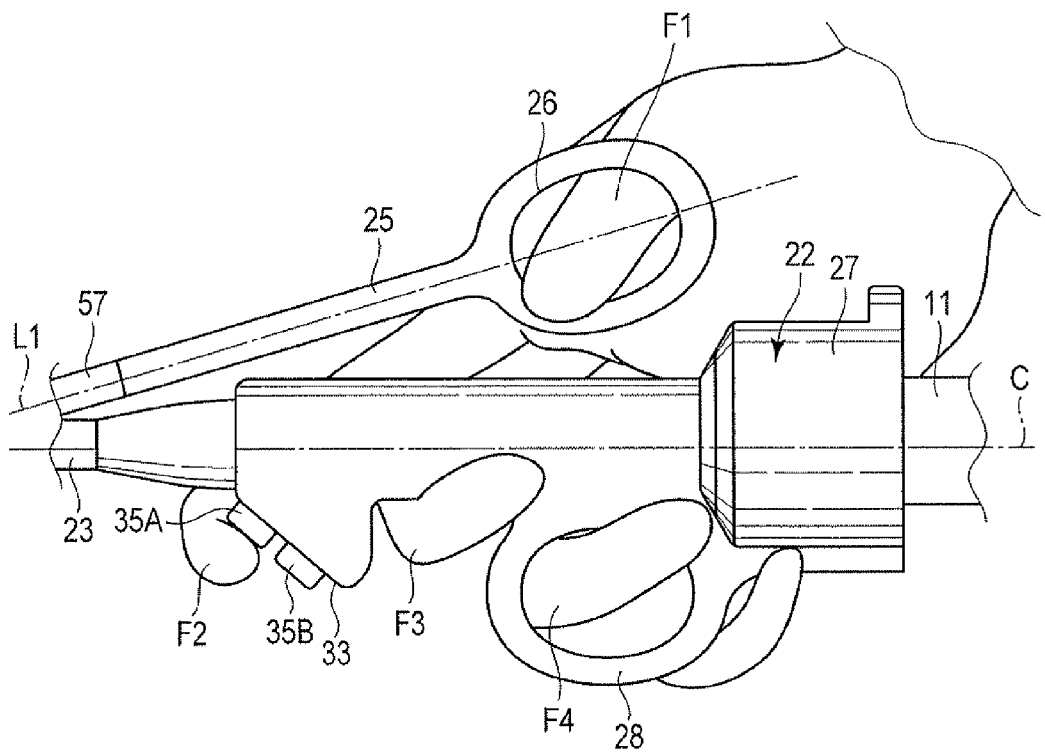
F I G. 12
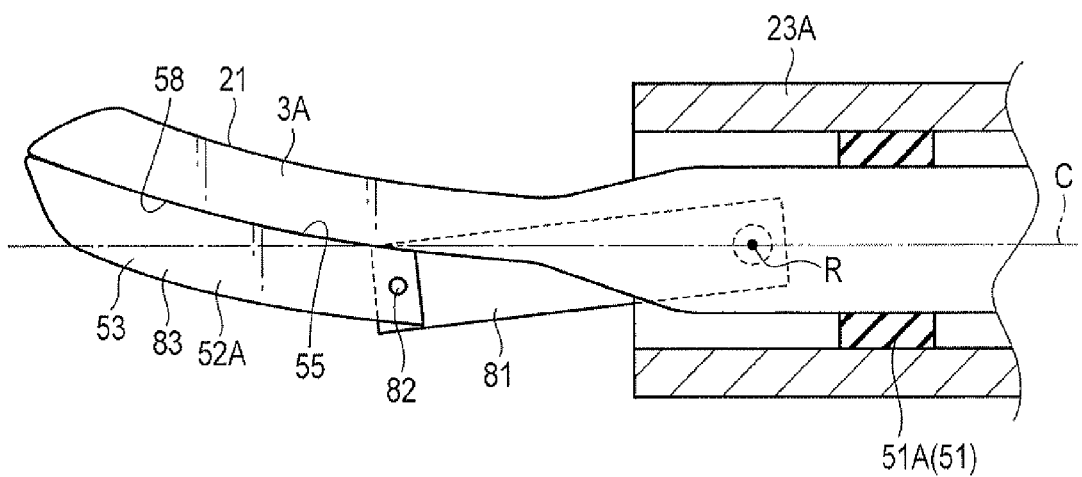
F I G. 13

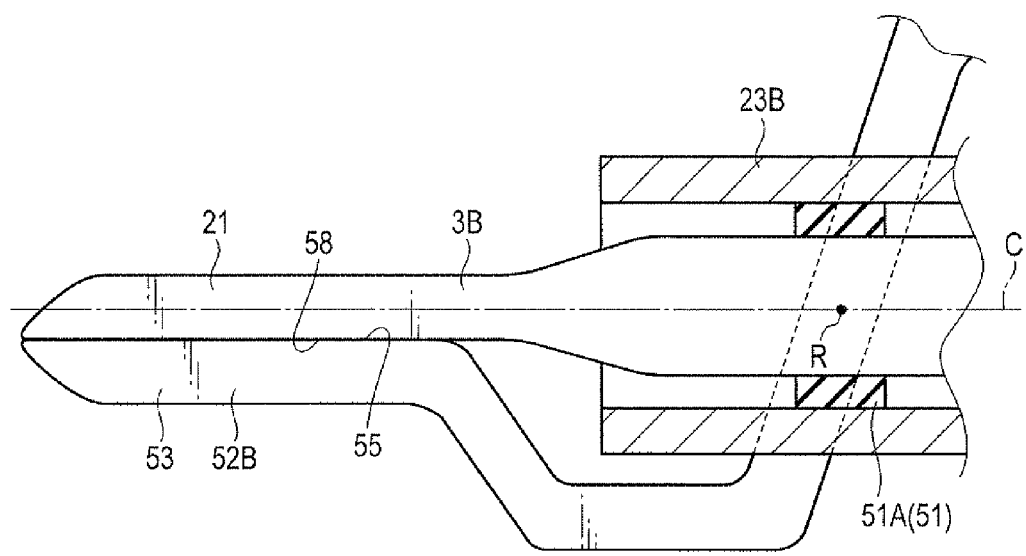
F I G. 14
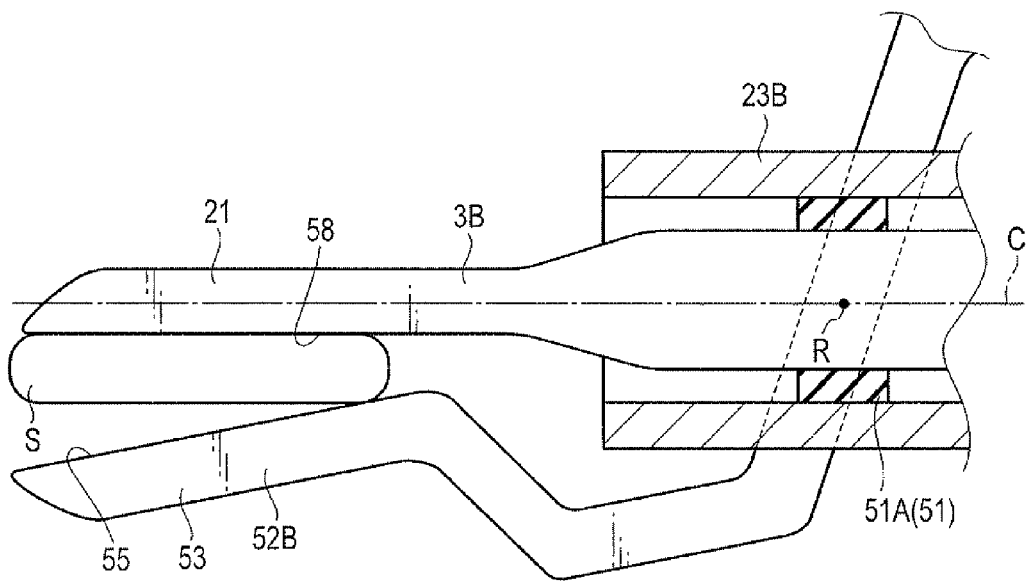
F I G. 15

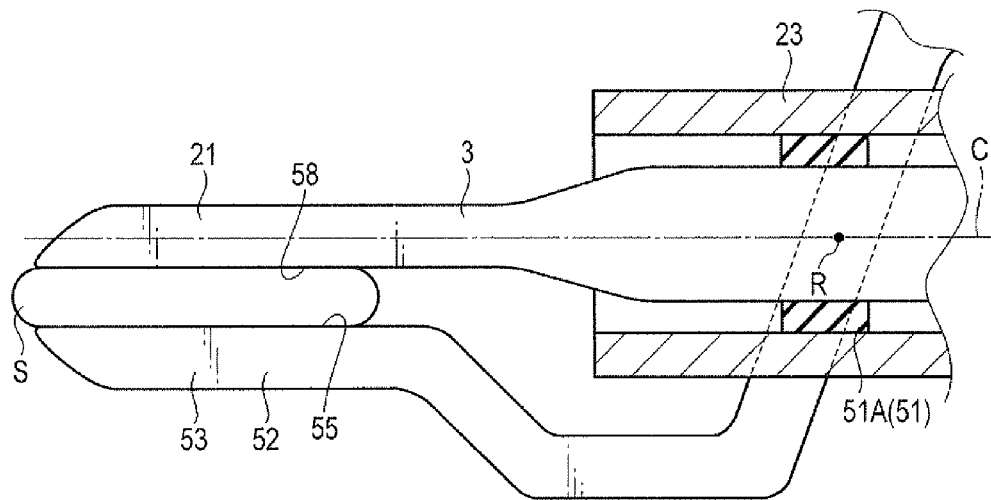
F I G. 16
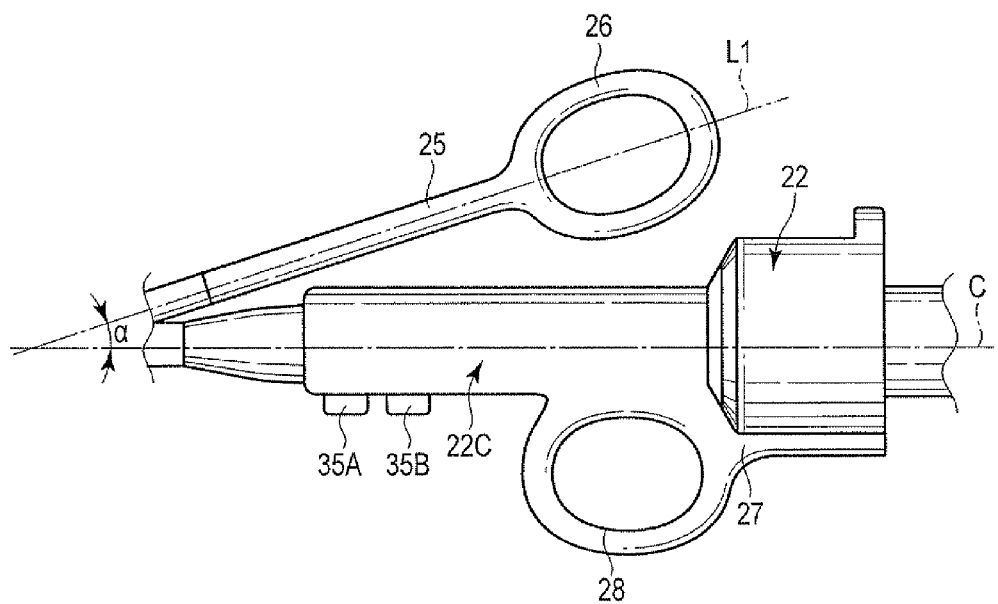
F I G. 17

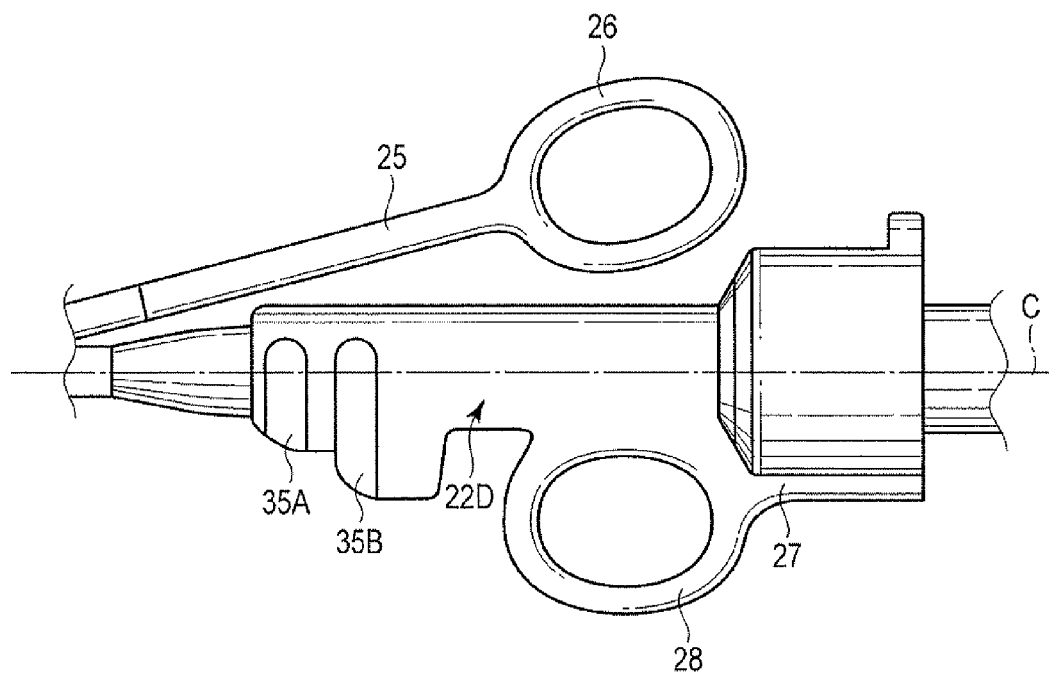
F I G. 18
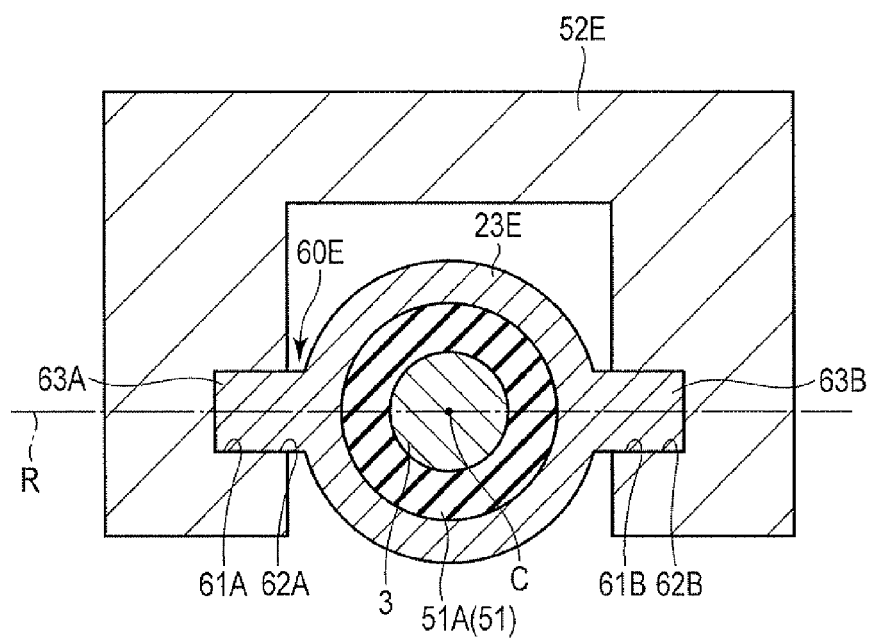
F I G. 19

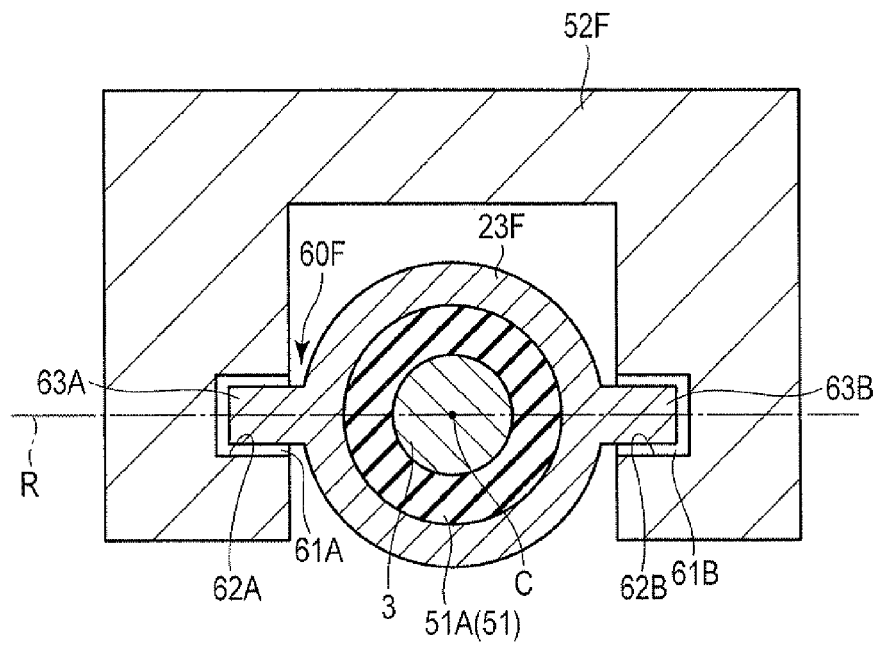
F I G. 20
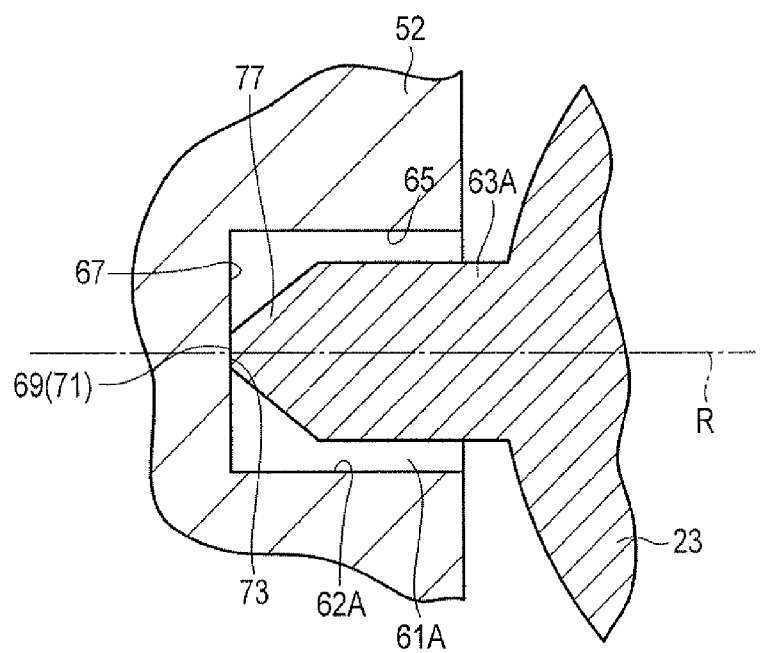
F I G. 21

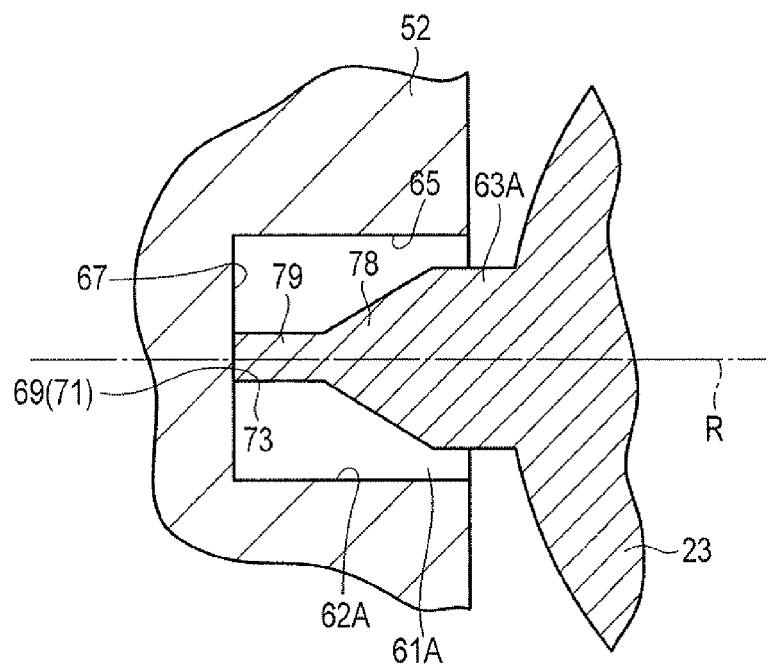
F I G. 22
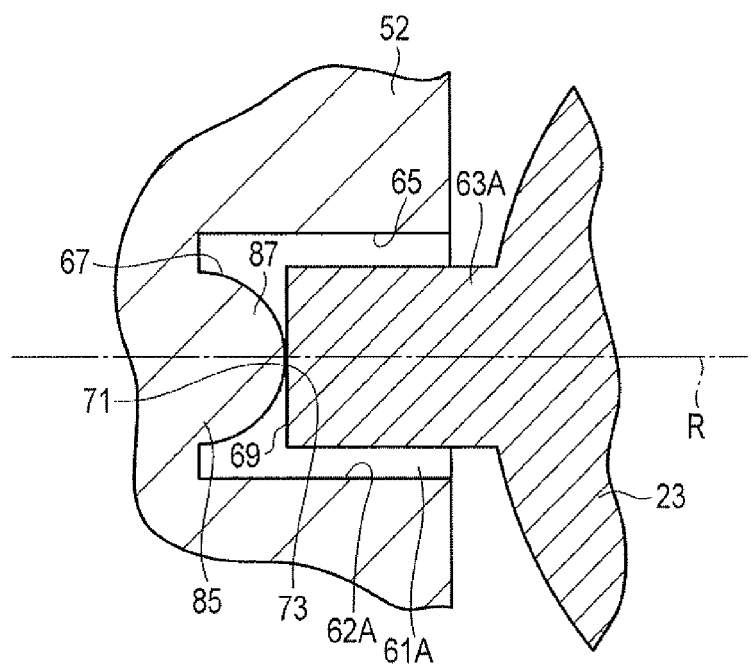
F I G. 23

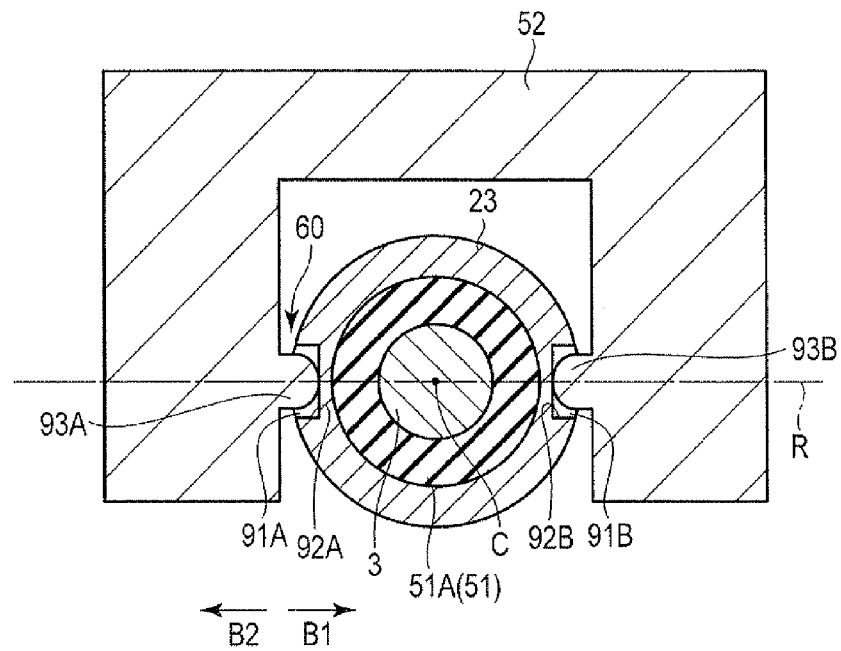
F I G. 24
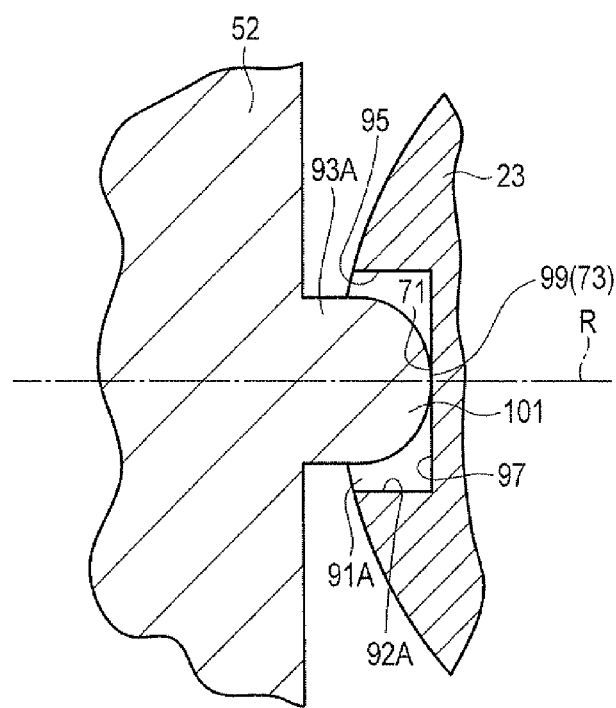
F I G. 25

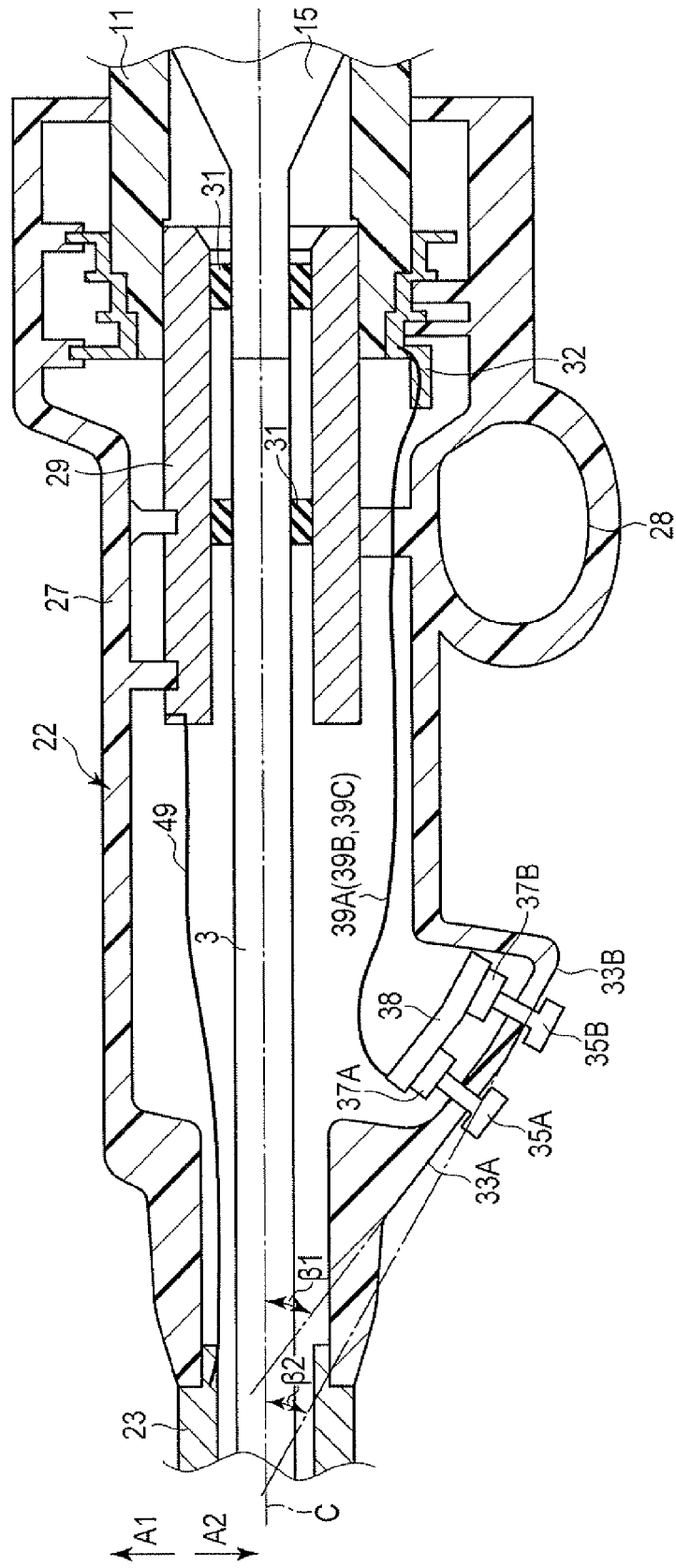
F I G. 27B

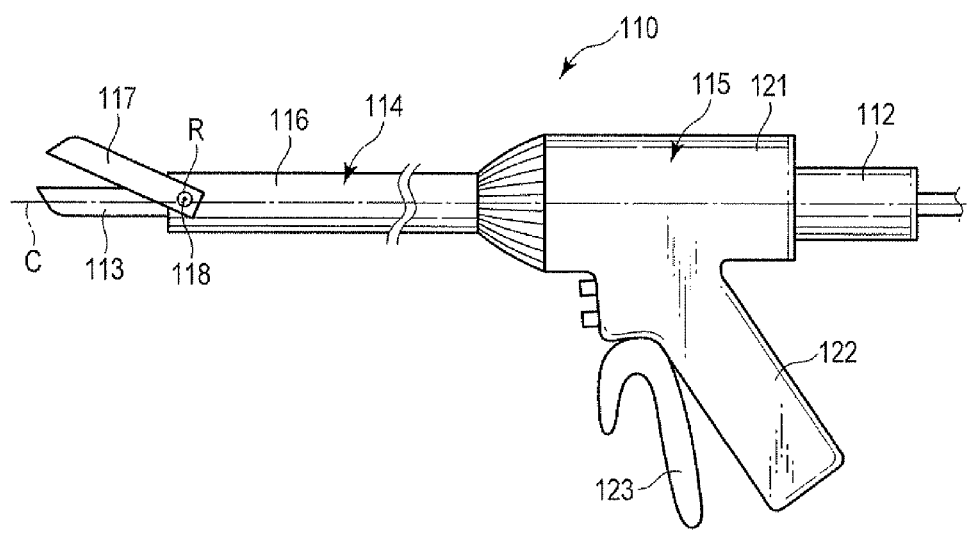
F I G. 28
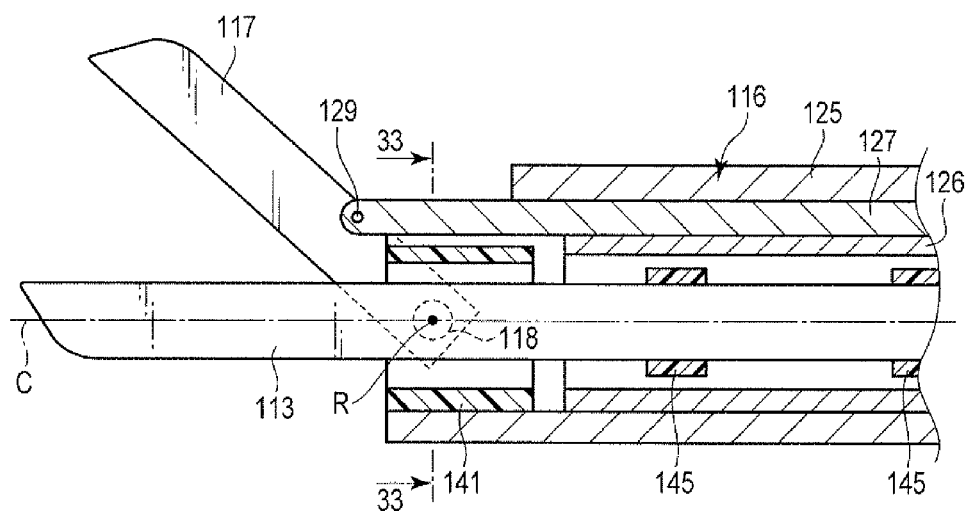
F I G. 29

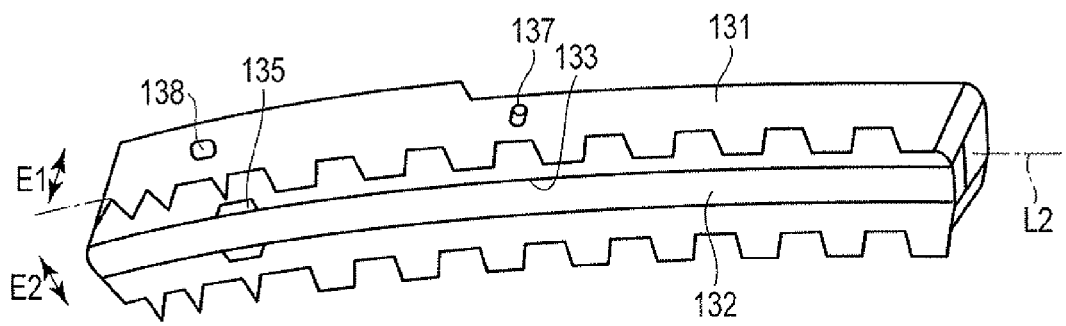
F I G. 30
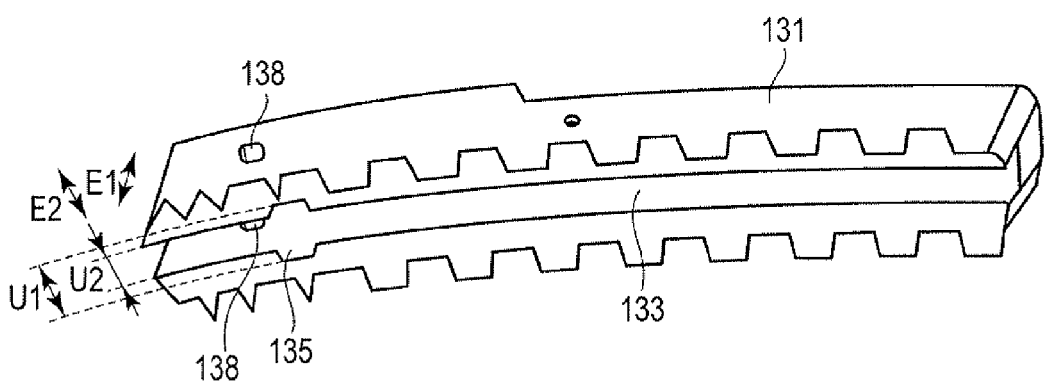
F I G. 31A
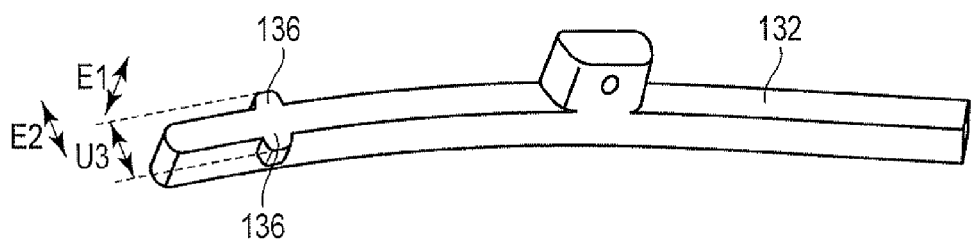
F I G. 31B

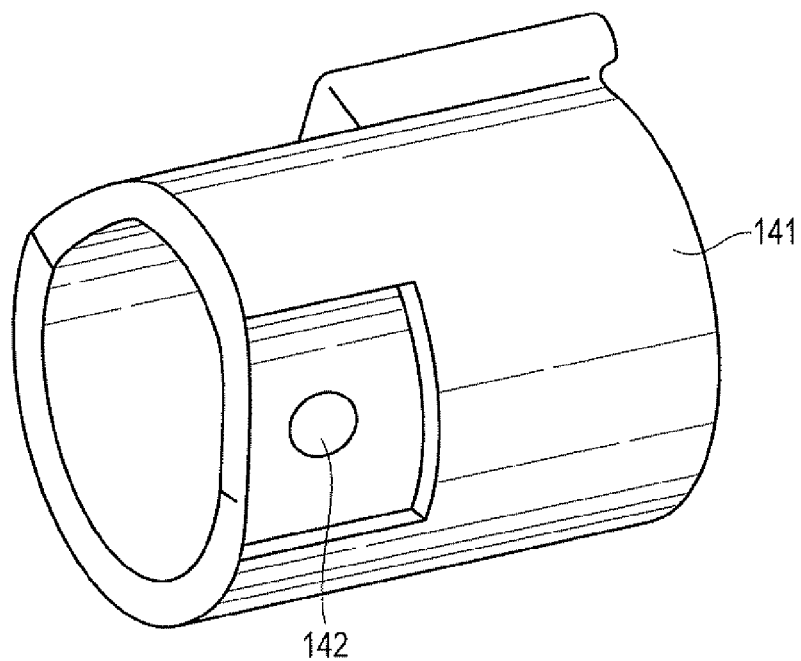
F I G. 32
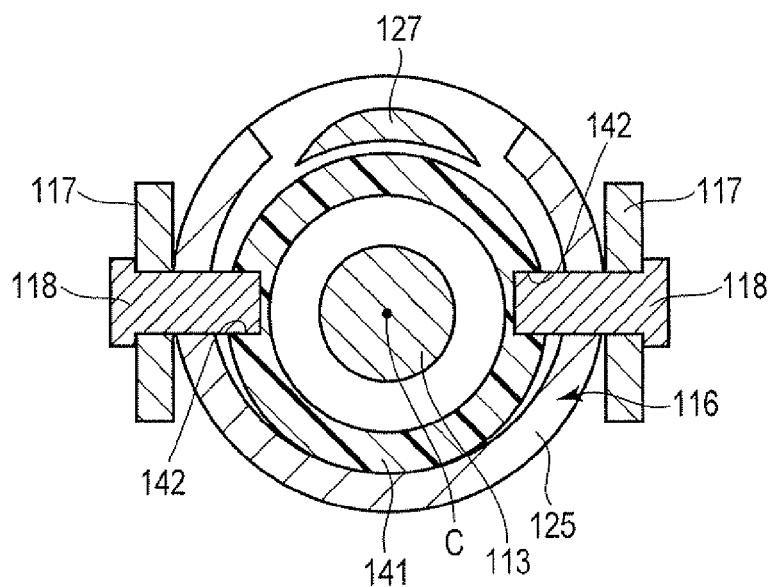
F I G. 33

US 8,652,132 B2

GRASPING TREATMENT DEVICE

CROSS-REFERENCE TO RELATED APPLICATIONS

This is a Continuation Application of PCT Application No. PCT/JP2012/057595, filed Mar. 23, 2012 and based upon and claiming the benefit of priority from prior U.S. Provisional Application No. 61/467,119, filed Mar. 24, 2011, the entire contents of which are incorporated herein by reference.

BACKGROUND OF THE INVENTION

1. Field of the Invention

The present invention relates to a grasping treatment device configured to perform a treatment by grasping a grasping target such as a living tissue between the distal portion of a probe and a jaw configured to open/close relative to the distal portion of the probe.

2. Description of the Related Art

Jpn. PCT National Publication No. 2009-514566 has disclosed an ultrasonic device, which is a grasping treatment device, including a probe configured to transmit ultrasonic waves, and a jaw configured to open/close relative to the distal portion of the probe. In this ultrasonic device, a scissors-like handle unit is opened/closed to grasp a grasping target such as a living tissue between the distal portion of the probe and the jaw, and thereby performs a treatment of the grasping target.

Jpn. Pat. Appln. KOKAI Publication No. 2009-261911 has disclosed an ultrasonic coagulation-and-cutting device, which is a grasping treatment device, including a probe configured to transmit ultrasonic waves and a jaw configured to open/close relative to the distal portion of the probe. This ultrasonic coagulation-and-cutting device is also used as a bipolar treatment device, which uses the distal portion of the probe as a first electrode portion and the jaw as a second electrode portion, to perform a bipolar treatment by a high-frequency current between the distal portion of the probe and the jaw. In this ultrasonic coagulation-and-cutting device, the jaw includes a jaw body rotatably attached to a sheath, and a wiper member attached to the jaw body via a pin. The wiper member is rotatable relative to the jaw body around the pin.

BRIEF SUMMARY OF THE INVENTION

According to one aspect of the invention, a grasping treatment device includes that a probe extending along a longitudinal axis; a sheath through which the probe is inserted so that the probe protrudes toward a distal direction; a jaw which is attached to a distal portion of the sheath rotatably around a rotation axis perpendicular to the longitudinal axis, and which is configured to open/close relative to a distal portion of the probe in open/close directions perpendicular to the longitudinal axis and perpendicular to the rotation axis; and a support member which is provided between the probe and the sheath, and which is configured to prevent contact between the probe and the sheath, wherein the support member includes a most-distal support member which is located on the most distal direction side, the position of the most-distal support member coinciding with the rotation axis of the jaw in directions parallel to the longitudinal axis.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing a medical treatment device according to a first embodiment of the present invention;

FIG. 2 is a schematic sectional view showing the configuration of a vibrator unit according to the first embodiment;

FIG. 3 is a partially sectional schematic side view showing the configuration of a probe according to the first embodiment;

FIG. 5 is a schematic diagram showing the electric connection between a vibrator case, a cylindrical member, and an electric connection ring according to the first embodiment;

FIG. 6 is a schematic sectional view showing a state in which the probe is inserted through a sheath according to the first embodiment;

FIG. 7 is a sectional view taken along the line VII-VII of FIG. 6;

FIG. 12 is a schematic diagram showing a state in which an operator grasps the fixed handle and a movable handle during a treatment with the medical treatment device according to the first embodiment;

FIG. 13 is a schematic diagram showing a state in which a jaw is in abutment with a first electrode portion of a probe according to a first comparative example;

FIG. 14 is a schematic diagram showing a state in which probe facing portion of a jaw and a jaw facing portion of the probe according to a second comparative example are parallel to each other;

FIG. 15 is a schematic diagram showing a state in which a living tissue is grasped between the jaw and a first electrode portion of the probe according to the second comparative example;

FIG. 16 is a schematic diagram showing a state in which the living tissue is grasped between the jaw and the first electrode portion of the probe according to the first embodiment;

FIG. 17 is a schematic side view showing a fixed handle and the movable handle according to a third comparative example;

FIG. 18 is a schematic side view showing a fixed handle and the movable handle according to a fourth comparative example;

FIG. 19 is a schematic sectional view showing the configuration of an electric contact unit according to a fifth comparative example;

FIG. 20 is a schematic sectional view showing the configuration of an electric contact unit according to a sixth comparative example;

FIG. 21 is a schematic sectional view showing the configurations of the first groove defining portion and the first projection of the electric contact unit according to a first modification;

FIG. 22 is a schematic sectional view showing the configurations of the first groove defining portion and the first projection of the electric contact unit according to a second modification;

FIG. 23 is a schematic sectional view showing the configurations of the first groove defining portion and the first projection of the electric contact unit according to a third modification;

FIG. 24 is a schematic sectional view showing the configuration of the electric contact unit according to a fourth modification;

FIG. 25 is a schematic sectional view showing the configurations of the first groove defining portion and the first projection of the electric contact unit according to the fourth modification;

FIG. 27B is a schematic sectional view showing the configuration of the inside of the fixed handle according to a sixth modification;

FIG. 28 is a schematic diagram showing a medical treatment device according to a first referential example;

FIG. 29 is a schematic sectional view showing the configurations of a probe and a sheath unit according to the first referential example;

FIG. 30 is a schematic perspective view showing the configuration of a jaw according to the first referential example;

FIG. 31A is a schematic perspective view showing the configuration of a jaw body of the jaw according to the first referential example;

FIG. 31B is a schematic perspective view showing the configuration of an elastic member of the jaw according to the first referential example;

FIG. 32 is a schematic perspective view showing the configuration of a probe protecting member according to the first referential example;

FIG. 33 is a sectional view taken along the line 33-33 of FIG. 29;

DETAILED DESCRIPTION OF THE INVENTION

First Embodiment

Figure 4:
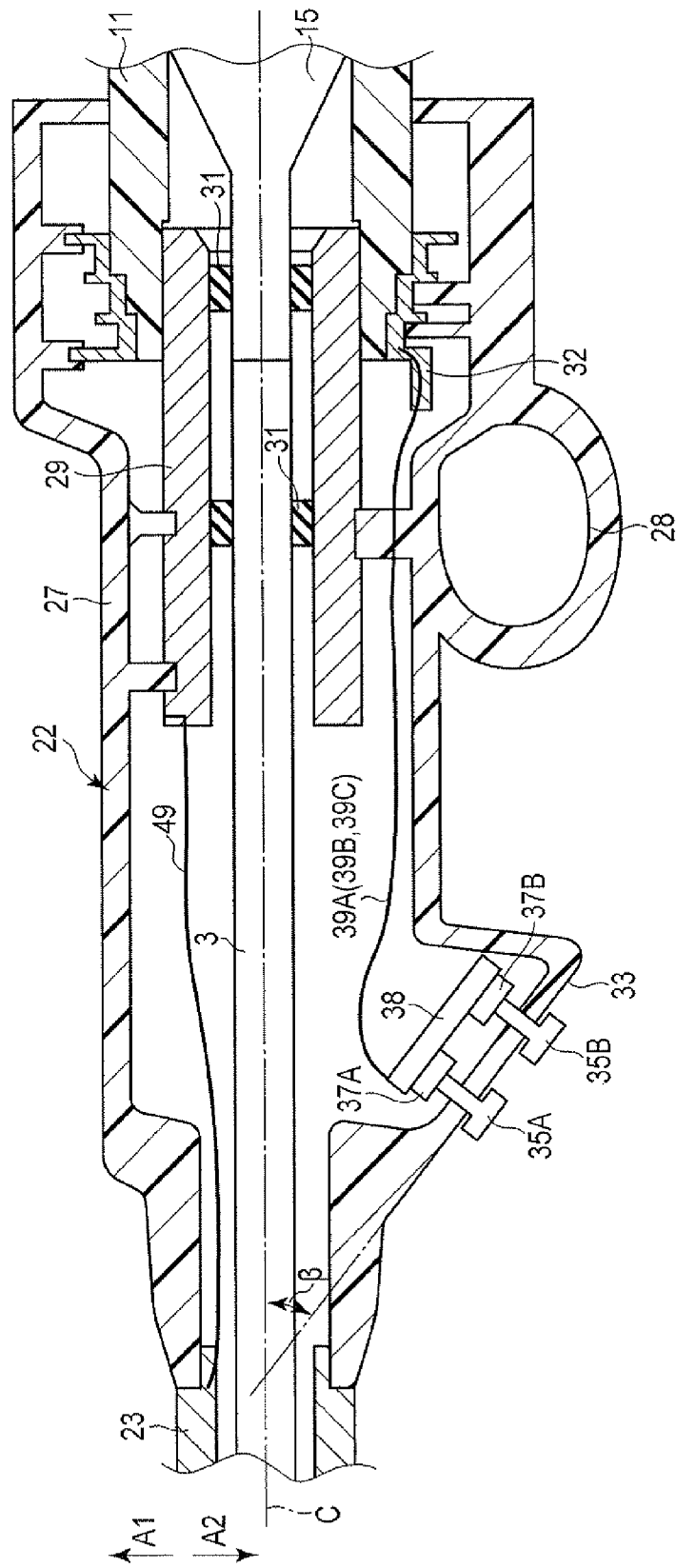
FIG. 4 is a schematic sectional view showing the configuration of the inside of a fixed handle according to the first embodiment.

A first embodiment of the present invention is described with reference to FIG. 1 to FIG. 20. FIG. 1 is a diagram showing a medical treatment device 1 according to the present embodiment. This medical treatment device 1 is a grasping treatment device which is configured to grasp a grasping target such as a living tissue between a distal portion of a probe 3 (described later) and a jaw 52 (described later) and configured to treat the grasped grasping target using an energy such as ultrasonic waves, high-frequency waves, or heat. The medical treatment device 1 according to the present embodiment is used as a bipolar treatment device which is configured to use the distal portion of the probe 3 and the jaw 52 as electrodes to perform a treatment by a high-frequency current. The medical treatment device 1 is also used as an ultrasonic treatment device which is configured to perform a treatment by ultrasonic vibrations. As shown in FIG. 1, the medical treatment device 1 includes a vibrator unit 2, the probe 3, a sheath unit 4, and a movable handle unit 5.

The vibrator unit 2 includes a vibrator case 11. One end of a cable 6 is connected to a proximal end of the vibrator case 11. The other end of the cable 6 is connected to a power supply unit 7. The power supply unit 7 includes an ultrasonic controller 8 and a high-frequency current controller 9.

FIG. 2 is a diagram showing the configuration of the vibrator unit 2. As shown in FIG. 2, an ultrasonic vibrator 12, which includes a piezoelectric element configured to convert a current to ultrasonic vibrations, is provided inside the vibrator case 11. One end of each of electric signal lines 13A and 13B is connected to the ultrasonic vibrator 12. The other end of each of the electric signal lines 13A and 13B is connected to the ultrasonic controller 8 of the power supply unit 7 through the cable 6. Ultrasonic vibrations are generated in the ultrasonic vibrator 12 by supplying a current to the ultrasonic vibrator 12 from the ultrasonic controller 8 via the electric signal lines 13A and 13B. A horn 15, which is configured to increase the amplitude of the ultrasonic vibrations, is coupled to a distal direction side of the ultrasonic vibrator 12.

The horn 15 is attached to the vibrator case 11, and electrically insulated from the vibrator case 11. An internal thread 16 is formed in a distal portion of the horn 15. In addition to the electric signal lines 13A and 13B, an electric signal line 17, extending from the high-frequency current controller 9 of the power supply unit 7 through the cable 6, is connected to the ultrasonic vibrator 12.

FIG. 3 is a diagram showing the configuration of the probe 3. As shown in FIG. 3, the probe 3 extends in the form of a column along a longitudinal axis C. An external thread 19 is provided in a proximal portion of the probe 3. When the external thread 19 of the probe 3 is screwed to the internal thread 16 of the horn 15, the probe 3 is attached to the horn 15.

When the probe 3 is attached to the horn 15, the ultrasonic vibrations generated in the ultrasonic vibrator 12 are transmitted to a distal end of the probe 3 via the horn 15. That is, the ultrasonic vibrations are transmitted from a proximal end to the distal end in the probe 3. The ultrasonic vibrations are longitudinal vibrations in which a vibration transmission direction and a vibration direction are the same directions.

Moreover, when the probe 3 is attached to the horn 15, a probe side current path of the high-frequency current is formed from the high-frequency current controller 9 to the distal portion of the probe 3 through the electric signal line 17, the ultrasonic vibrator 12, and the horn 15. A first electrode portion 21 is provided in the distal portion of the probe 3. That is, the high-frequency current is transmitted by the probe side current path between the high-frequency current controller 9 and the first electrode portion 21 along the longitudinal axis C.

As shown in FIG. 1, the sheath unit 4 extends along the longitudinal axis C. The sheath unit 4 includes a fixed handle 22, and a sheath 23 attached to the distal direction side of the fixed handle 22. The movable handle unit 5 includes a movable handle 25 configured to open/close relative to the fixed handle 22. The movable handle 25 includes a movable handle ring 26 which is a movable side finger placing portion. The movable handle 25 is configured to open/close relative to the fixed handle 22 in a first open/close direction (first direction) perpendicular to the longitudinal axis C, indicated by the arrow A1 in FIG. 1, and in a second open/close direction (second direction) opposite to the first open/close direction, indicated by the arrow A2 in FIG. 1. The movable handle 25 is located to the first open/close direction side of the fixed handle 22. An axis L1 of the movable handle 25 is inclined at an acute angle $\alpha$ to the longitudinal axis C.

The fixed handle 22 includes an exterior handle casing 27. A fixed handle ring 28, which is a fixed side finger placing portion, is provided in a part of the handle casing 27 (fixed handle 22) on the second open/close direction side. The sheath 23 is provided to an outer peripheral direction side of the probe 3. The probe 3 is inserted through the sheath 23 so that the first electrode portion 21 protrudes toward the distal direction from the sheath 23.

FIG. 4 is a diagram showing the configuration of the inside of the fixed handle 22. As shown in FIG. 4, a cylindrical member 29 is fixed to the handle casing 27 of the fixed handle 22. A proximal end of the probe 3 extends into the cylindrical member 29. The probe 3 is attached to the horn 15 inside the cylindrical member 29. The probe 3 and the horn 15 are supported by the cylindrical member 29 via an insulating member 31. This prevents the probe 3 and the horn 15 from contacting the cylindrical member 29, and electrically insulates the probe 3 and the horn 15 from the cylindrical member 29.

An electric connection ring 32 is provided to the outer peripheral direction side of the cylindrical member 29. The electric connection ring 32 is provided to be fixed to the handle casing 27. A distal portion of the vibrator case 11 is engaged between the cylindrical member 29 and the electric connection ring 32. The distal portion of the vibrator case 11 is engaged between the cylindrical member 29 and the electric connection ring 32, and the vibrator case 11 is thereby coupled to the fixed handle 22 (the sheath unit 4). When the vibrator case 11 is coupled to the fixed handle 22, an outer peripheral portion of the distal portion of the vibrator case 11 is in contact with the electric connection ring 32, and an inner peripheral portion of the distal portion of the vibrator case 11 is in contact with the cylindrical member 29.

An inclined plane 33 inclined relative to the longitudinal axis C is provided in a part of the handle casing 27 (fixed handle 22) on the second open/close direction (direction indicated by the arrow A2 in FIG. 1 and FIG. 4) side. This inclined plane 33 is provided to the distal direction side of the fixed handle ring 28. In the inclined plane 33, it goes toward the proximal direction side as it goes from the first open/close direction (direction indicated by the arrow A1 in FIG. 1 and FIG. 4) to the second open/close direction. In other words, the inclined plane 33 is an ascending slope as it goes from the distal direction toward the proximal direction in the handle casing 27. Therefore, the angle between the inclined plane 33 and the longitudinal axis C is an acute angle $\beta$. This acute angle $\beta$ is preferably 60° to 70°, and particularly preferably 65°.

Input buttons 35A and 35B, which are two operation input sections, are provided in the inclined plane 33. Each of the input buttons 35A and 35B is pressed to input the operation by an operator. The input buttons 35A and 35B are pressed in a direction perpendicular to the inclined plane 33. Switches 37A and 37B and an electric circuit board 38 are provided to an inner peripheral direction side of the inclined plane 33. The switch 37A is turned on/off by an input operation in the input button 35A. Similarly, the switch 37B is turned on/off by an input operation in the input button 35B.

FIG. 5 is a schematic diagram showing the electric connection between the vibrator case 11, the cylindrical member 29, and the electric connection ring 32. As shown in FIG. 4 and FIG. 5, three electric signal lines 39A to 39C are provided in the handle casing 27. The electric signal line 39A is electrically connected to the switch 37A via the electric circuit board 38. The electric signal line 39B is electrically connected to the switch 37B via the electric circuit board 38. The electric signal line 39C is electrically connected to the switch 37A and the switch 37B via the electric circuit board 38. The electric signal line 39C is a common line shared as a ground line of the switch 37A and the switch 37B.

The electric connection ring 32 includes a first electric connection portion 42A, a second electric connection portion 42B, and a third electric connection portion 42C. The first electric connection portion 42A is electrically insulated from the second electric connection portion 42B. The second electric connection portion 42B is electrically insulated from the third electric connection portion 42C. The first electric connection portion 42A is electrically insulated from the third electric connection portion 42C. The electric signal line 39A is connected to the first electric connection portion 42A. The electric signal line 39B is connected to the second electric connection portion 42B. The electric signal line 39C is connected to the third electric connection portion 42C.

The vibrator case 11 includes a first electric conducting portion 43A, a second electric conducting portion 43B, and a third electric conducting portion 43C. The first electric conducting portion 43A, the second electric conducting portion 43B, and the third electric conducting portion 43C extend along the longitudinal axis C. The first electric conducting portion 43A is electrically insulated from the second electric conducting portion 43B. The second electric conducting portion 43B is electrically insulated from the third electric conducting portion 43C. The first electric conducting portion 43A is electrically insulated from the third electric conducting portion 43C. When the vibrator case 11 is coupled to the fixed handle 22 (the sheath unit 4), a distal portion of the first electric conducting portion 43A alone is in electric contact with the first electric connection portion 42A of the electric connection ring 32. Similarly, a distal portion of the second electric conducting portion 43B alone is in electric contact with the second electric connection portion 42B of the electric connection ring 32. A distal portion of the third electric conducting portion 43C alone is in electric contact with the third electric connection portion 42C of the electric connection ring 32.

One end of an electric signal line 45 is connected to a proximal portion of the first electric conducting portion 43A. One end of an electric signal line 46 is connected to a proximal portion of the second electric conducting portion 43B. One end of an electric signal line 47 is connected to a proximal portion of the third electric conducting portion 43C. The other ends of the electric signal lines 45 to 47 are connected to the power supply unit 7 through the cable 6.

As described above, a first electric signal path is formed from the switch 37A to the power supply unit 7 through the electric signal line 39A, the first electric connection portion 42A, the first electric conducting portion 43A, and the electric signal line 45. A second electric signal path is formed from the switch 37B to the power supply unit 7 through the electric signal line 39B, the second electric connection portion 42B, the second electric conducting portion 43B, and the electric signal line 46. Moreover, a ground path is formed from the switch 37A and the switch 37B to the power supply unit 7 through the electric signal line 39C, the third electric connection portion 42C, the third electric conducting portion 43C, and the electric signal line 47.

If the input button 35A is pressed, the switch 37A is turned on, and the first electric signal path is electrically connected to the ground path by the switch 37A. As a result, an electric signal is transmitted to the power supply unit 7 from the switch 37A. A current is then supplied to the ultrasonic vibrator 12 from the ultrasonic controller 8 via the electric signal lines 13A and 13B, and ultrasonic vibrations are generated in the ultrasonic vibrator 12. At the same time, the condition is switched so that a high-frequency current is output from the high-frequency current controller 9. If the input button 35B is pressed, the switch 37B is turned on, and the second electric signal path is electrically connected to the ground path by the switch 37B. As a result, an electric signal is transmitted to the power supply unit 7 from the switch 37B. A high-frequency current is then output from, for example, the high-frequency current controller 9 alone, and the condition is switched so that no ultrasonic vibrations are generated.

As shown in FIG. 5, the vibrator case 11 includes a fourth electric conducting portion 43D extending along the longitudinal axis C. All of the first electric conducting portion 43A, the second electric conducting portion 43B, and the third electric conducting portion 43C are electrically insulated from the fourth electric conducting portion 43D. An electric signal line 48 extending from the high-frequency current controller 9 of the power supply unit 7 through the cable 6 is connected to a proximal portion of the fourth electric conducting portion 43D. When the vibrator case 11 is coupled to the fixed handle 22 (the sheath unit 4), a distal portion of the fourth electric conducting portion 43D alone is in electric contact with the cylindrical member 29.

As shown in FIG. 4, one end of an electric signal line 49 is connected to the cylindrical member 29. The other end of the electric signal line 49 is connected to the sheath 23. In this way, the high-frequency current is transmitted between the high-frequency current controller 9 and the sheath 23 via the electric signal line 48, the fourth electric conducting portion 43D, and the electric signal line 49.

FIG. 6 is a diagram showing a state in which the probe 3 is inserted through the sheath 23. As shown in FIG. 6, a support member 51 is provided between the probe 3 and the sheath 23. The support member 51 is made of an insulating material. The contact between the probe 3 and the sheath 23 is prevented by the support member 51, and the probe 3 is electrically insulated from the sheath 23. In the present embodiment, the support member 51 is located at the node position of ultrasonic waves. This more effectively prevents the contact between the probe 3 and the sheath 23. One or more support members 51 may be provided, and at least one support member 51 has only to be provided.

The movable handle unit 5 includes the jaw 52 rotatably attached to a distal portion of the sheath 23, and an intermediary member 57 provided between the movable handle 25 and the jaw 52. The jaw 52 is attached to the sheath 23, and the movable handle unit 5 is coupled to the sheath unit 4. The jaw 52 is configured to open/close relative to the first electrode portion 21 provided to the distal portion of the probe 3. The jaw 52 includes a second electrode portion 53 located to the second open/close direction (direction indicated by the arrow A2 in FIG. 1 and FIG. 6) side of the first electrode portion 21 of the probe 3. The second electrode portion 53 is electrically connected to the sheath 23. A probe facing portion 55, which faces the first electrode portion 21 of the probe 3, is provided in a part of an external surface of the second electrode portion 53 (jaw 52) on the first open/close direction (direction indicated by the arrow A1 in FIG. 1 and FIG. 6) side. Similarly, a jaw facing portion 58, which faces the second electrode portion 53 of the jaw 52, is provided in a part of an external surface of the first electrode portion 21 of the probe 3 on the second open/close direction side.

The movable handle unit 5 rotates around a coupling portion with the sheath 23 as a rotation axis R. The rotation axis R is perpendicular to the longitudinal axis C and perpendicular to the first open/close direction and the second open/close direction. Therefore, if the movable handle 25 is moved in the first open/close direction to open the movable handle 25 relative to the fixed handle 22, the jaw 52 moves in the second open/close direction. As a result, the jaw 52 is positioned to be open relative to the first electrode portion 21. On the other hand, if the movable handle 25 is moved in the second open/close direction to close the movable handle 25 relative to the fixed handle 22, the jaw 52 moves in the first open/close direction. As a result, the jaw 52 is positioned to be closed relative to the first electrode portion 21. That is, the jaw 52 rotates relative to the sheath 23 around the rotation axis R, and thereby opens/closes relative to the first electrode portion 21 of the probe 3 between the open position and the closed position.

As described above, the second electrode portion 53 is electrically connected to the sheath 23. Thus, a high-frequency current is transmitted between the sheath 23 and the second electrode portion 53. A high-frequency current is also transmitted between the high-frequency current controller 9 and the sheath 23 via the electric signal line 48, the fourth electric conducting portion 43D, and the electric signal line 49. Accordingly, a jaw side current path is formed from the high-frequency current controller 9 to the second electrode portion of the jaw 52 through the electric signal line 48, the fourth electric conducting portion 43D, the electric signal line 49, and the sheath 23. That is, the high-frequency current is transmitted between the high-frequency current controller 9 and the second electrode portion 53 by the jaw side current path.

An external surface of the sheath 23 and the parts of external surface of the jaw 52 other than the probe facing portion 55 are coated with, for example, an insulating material. This prevents an electric shock even when, for example, a hand of the operator touches the external surface of the sheath 23 and the external surface of the jaw 52. The intermediary member 57 between the jaw 52 and the movable handle 25 is made of an insulating material. This prevents the transmission of a high-frequency current from the jaw 52 to the movable handle 25.

FIG. 7 is a sectional view taken along the line VII-VII of FIG. 6. As shown in FIG. 6 and FIG. 7, in directions parallel to the longitudinal axis C, a position where the jaw 52 is coupled to the sheath 23 coincides with a position of a most-distal support member 51A which is the support member 51 located on the most distal direction side. That is, in the directions parallel to the longitudinal axis C, a position of the rotation axis R of the jaw 52 coincides with the position of the most-distal support member 51A.

Figure 8:
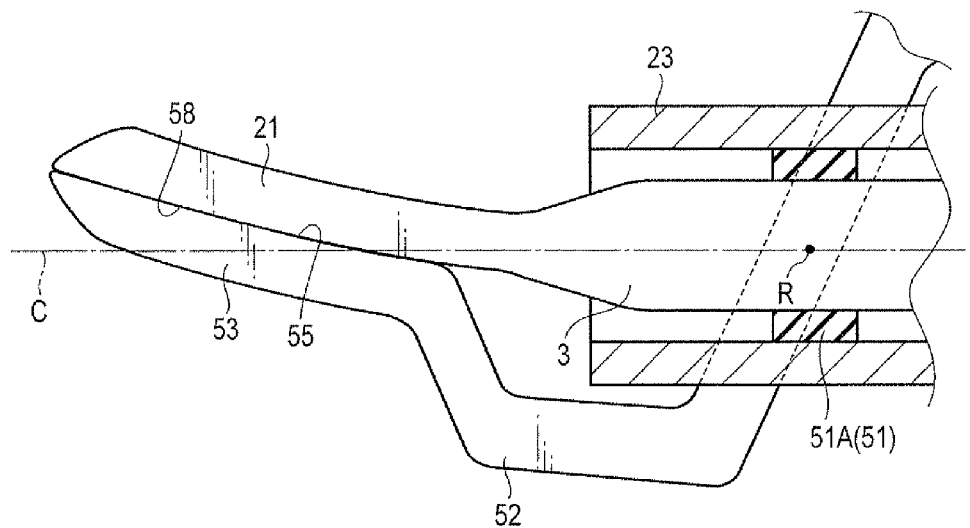
FIG. 8 is a schematic diagram showing a state in which a jaw is in abutment with a first electrode portion of the probe according to the first embodiment.

FIG. 8 is a diagram showing a state in which the jaw 52 is in abutment with the first electrode portion 21 of the probe 3 and a press force (grasping force) resulting from the jaw 52 acts on the probe 3. As described above, the jaw 52 moves (rotates) in the first open/close direction, and thereby closes relative to the first electrode portion 21. As shown in FIG. 8, the jaw 52 then abuts on the first electrode portion 21 of the probe 3. Accordingly, a part of the probe 3 provided to the distal direction side of the most-distal support member 51A deflects. Here, the deflecting amount of the probe 3 at the position of the most-distal support member 51A in the directions parallel to the longitudinal axis C is always zero. Therefore, in the directions parallel to the longitudinal axis C, the position where the deflecting amount of the probe 3 is always zero coincides with the position of the rotation axis R of the jaw 52. Thus, when the jaw 52 is in abutment with the first electrode portion 21 of the probe 3 and the part of the probe 3 provided to the distal direction side of the most-distal support member 51A deflects, the probe facing portion 55 of the jaw 52 abuts on the jaw facing portion 58 of the probe 3 with no space therebetween. That is, a uniform pressure is applied to the jaw facing portion 58 of the probe 3 by the probe facing portion 55 of the jaw 52. In the present embodiment, in the directions parallel to the longitudinal axis C, the position of the rotation axis R of the jaw 52 and the position of the most-distal support member 51A coincide with the node position of ultrasonic waves.

Figure 9:
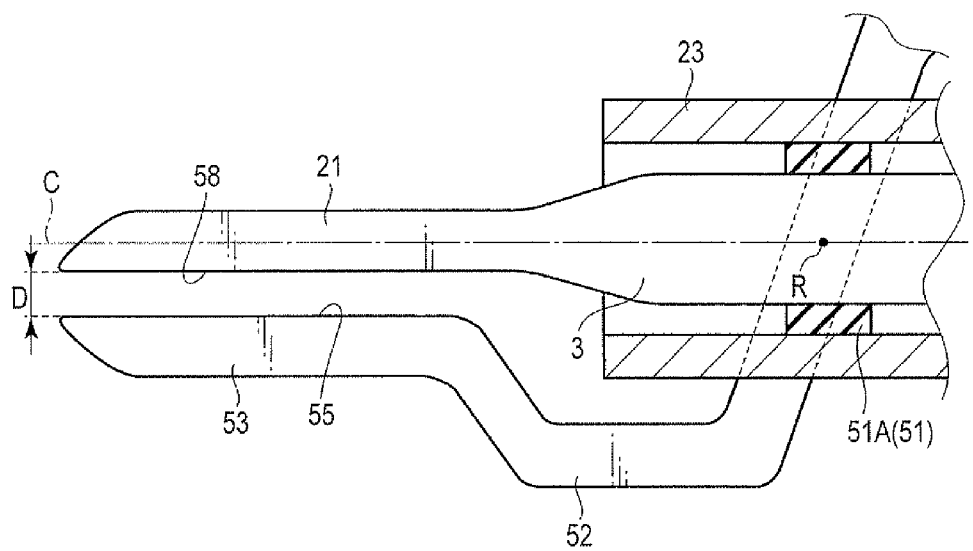
FIG. 9 is a schematic diagram showing a state in which a probe facing portion of the jaw and a jaw facing portion of the probe according to the first embodiment are parallel to each other.

FIG. 9 is a diagram showing a state in which the probe facing portion 55 of the jaw 52 and the jaw facing portion 58 of the probe 3 are parallel to each other. As shown in FIG. 9, when the jaw 52 closes relative to the first electrode portion 21, the probe facing portion 55 of the jaw 52 is parallel to the jaw facing portion 58 of the probe 3 with a predetermined distance B therebetween before abutting on the first electrode portion 21 of the probe 3. That is, when the probe facing portion 55 of the jaw 52 is parallel to the jaw facing portion 58 of the probe 3, the probe facing portion 55 is separate from the jaw facing portion 58 at the predetermined distance D.

As shown in FIG. 7, an electric contact unit 60 is provided between the sheath 23 and the jaw 52 to maintain constant transmission of the high-frequency current between the sheath 23 and the second electrode portion 53 of the jaw 52. This electric contact unit 60 has a function as a coupler configured to couple the sheath 23 to the jaw 52 to rotate the jaw 52 relative to the sheath 23 around the rotation axis R. In the electric contact unit 60, a first groove 61A and a second groove 61B, which are recessed toward the outer peripheral direction along the rotation axis R, are provided in the jaw 52. The first groove 61A is recessed toward a first rotation axis direction (direction indicated by the arrow B1 in FIG. 7) parallel to the rotation axis R. The second groove 61B is recessed toward a second rotation axis direction (direction indicated by the arrow B2 in FIG. 7) opposite to the first rotation axis direction. The first groove 61A is defined by a first groove defining portion 62A, and the second groove 61B is defined by a second groove defining portion 62B.

In the electric contact unit 60, a first projection 63A and a second projection 63B, which protrude toward the outer peripheral direction along the rotation axis R, are also provided in the outer peripheral portion of the sheath 23. The first projection 63A protrudes toward the first rotation axis direction, and the second projection 63B protrudes toward the second rotation axis direction. The first projection 63A is inserted in the first groove 61A, and the second projection 63B is inserted in the second groove 61B.

Figure 10:
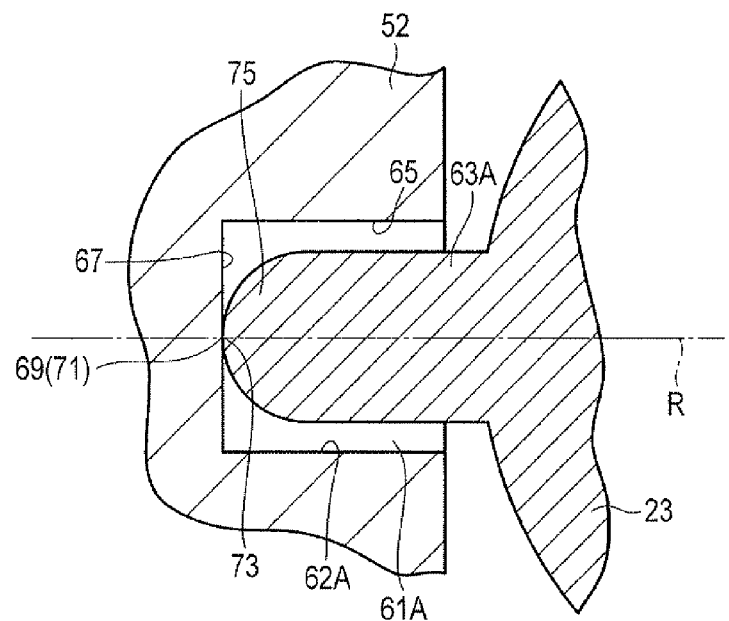
FIG. 10 is a schematic sectional view showing the configurations of a first groove defining portion and a first projection of an electric contact unit according to the first embodiment.

FIG. 10 is a diagram showing the configurations of the first groove defining portion 62A and the first projection 63A. Although the first groove defining portion 62A and the first projection 63A are only described below, the second groove defining portion 62B is similar in configuration to the first groove defining portion 62A, and the second projection 63B is similar in configuration to the first projection 63A. Therefore, the second groove defining portion 62B and the second projection 63B are not described.

As shown in FIG. 10, the first groove defining portion 62A includes a groove side surface 65 and a groove bottom surface 67. The first projection 63A includes a protruding end 69. The first projection 63A is inserted in the first groove 61A with a clearance between the first projection 63A and the groove side surface 65. A sheath side contact portion 71 is located in the protruding end 69. That is, the sheath side contact portion 71 is provided in the outer peripheral portion of the sheath 23. A jaw side contact portion 73 is located in the groove bottom surface 67 of the first groove defining portion 62A of the jaw 52. That is, the jaw side contact portion 73 is provided in the inner peripheral portion of the jaw 52. The jaw side contact portion 73 slidably contacts the sheath side contact portion 71. When the sheath side contact portion 71 contacts the jaw side contact portion 73, a high-frequency current is transmitted between the sheath 23 and the second electrode portion 53 of the jaw 52.

Figure 11:
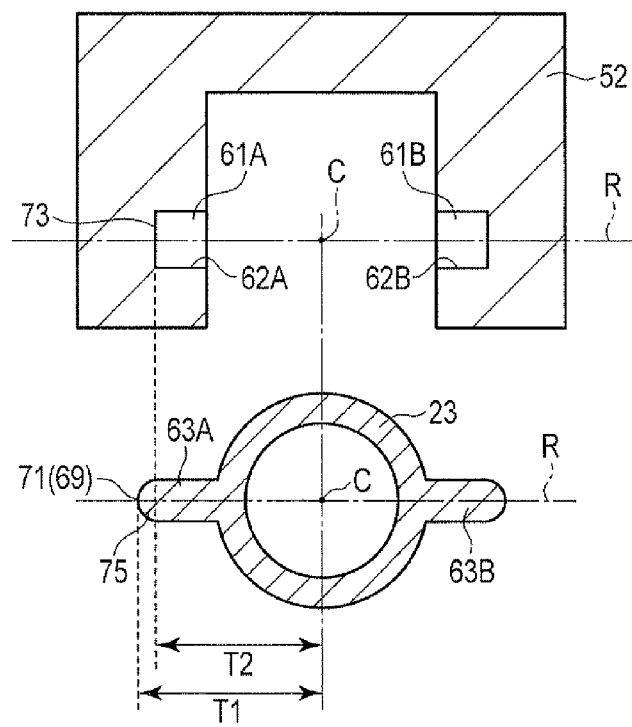
FIG. 11 is a schematic sectional view showing the sheath and the jaw when the jaw is not attached to the sheath according to the first embodiment.

FIG. 11 is a diagram showing the sheath 23 and the jaw 52 when the jaw 52 is not attached to the sheath 23. As shown in FIG. 11, when the jaw 52 is not attached to the sheath 23, a first dimension T1 along the rotation axis R from the longitudinal axis C to the sheath side contact portion 71 is greater than a second dimension T2 along the rotation axis R from the longitudinal axis C to the jaw side contact portion 73. This configuration maintains the constant contact between the jaw side contact portion 73 and the sheath side contact portion 71 even when a clearance is provided between the first projection 63A and the groove side surface 65 of the first groove defining portion 62A. Thus, transmission of a high-frequency current is maintained between the sheath 23 and the second electrode portion 53 of the jaw 52.

As shown in FIG. 10, the first projection 63A includes a projection side semispherical portion 75 semispherically provided to extend to the sheath side contact portion 71 along the rotation axis R. The projection side semispherical portion 75 is a projection side sectional changing portion, which is configured to decrease in the sectional area perpendicular to the rotation axis R as it goes toward the protruding end 69 of the first projection 63A along the rotation axis R. The area of contact between the sheath side contact portion 71 and the jaw side contact portion 73 is reduced by the projection side semispherical portion 75.

Now, the functions of the medical treatment device 1 according to the present embodiment are described. FIG. 12 is a diagram showing a state in which the operator grasps the fixed handle 22 and the movable handle 25 during a treatment with the medical treatment device 1. As shown in FIG. 12, when the fixed handle 22 and the movable handle 25 are grasped, a ring finger F4 is hooked to the fixed handle ring 28 of the fixed handle 22. A thumb F1 is hooked to the movable handle ring 26 of the movable handle 25. At the same time, a fore finger F2 and a middle finger F3 extend at a slant relative to the longitudinal axis C. That is, the extending directions of the fore finger F2 and the middle finger F3 are at the slant relative to the longitudinal axis C.

If the movable handle 25 is opened/closed relative to the fixed handle 22, the jaw 52 opens/closes relative to the first electrode portion 21 of the probe 3. As a result, the living tissue is grasped between the first electrode portion 21 of the probe 3 and the second electrode portion 53 of the jaw 52. An input operation is performed by the input buttons 35A and 35B, which are the operation input sections, while the fixed handle 22 and the movable handle 25 are grasped. In response to the input operation at the input buttons 35A and 35B, ultrasonic vibrations are generated, and a high-frequency current is supplied. If the input button 35A is pressed, for example, ultrasonic vibrations are generated in the ultrasonic vibrator 12, and at the same time, the condition is switched so that the high-frequency current is output from the high-frequency current controller 9. In this case, a grasped living tissue such as a blood vessel is cut by frictional heat generated by the ultrasonic vibrations of the probe 3. The living tissue is coagulated by the passage of the high-frequency current through the living tissue between the first electrode portion 21 and the second electrode portion 53. If the input button 35B is pressed, for example, a high-frequency current is output from the high-frequency current controller 9 alone, and the condition is switched so that no ultrasonic vibrations are generated. In this case, the living tissue between the first electrode portion 21 and the second electrode portion 53 is not cut, and is only coagulated by the high-frequency current.

Here, in the grasping treatment device shown in Jpn. PCT National Publication No. 2009-514566, the position of the rotation axis of the jaw does not coincide with the position of the most-distal support member in directions parallel to the longitudinal axis. Therefore, in the directions parallel to the longitudinal axis, the position where the deflecting amount of the probe is always zero does not coincide with the position of the rotation axis of the jaw. Thus, when the jaw is in abutment with the distal portion (first electrode portion) of the probe and the part of the probe provided to the distal direction side of the most-distal support member deflects, a clearance is produced between the jaw and the distal portion of the probe. In particular, a large clearance is produced in a part to the distal direction side of an abutment position between the jaw and the distal portion of the probe. The clearance produced between the jaw and the distal portion of the probe reduces the grasping force of grasping the living tissue and also reduces the frictional heat generated by the ultrasonic vibrations. As a result, the treatment performance deteriorates when the living tissue between the first electrode portion (the distal portion of the probe) and the second electrode portion (the jaw) is cut by the ultrasonic vibrations.

Accordingly, as a first comparative example, a probe 3A, a sheath 23A, and a jaw 52A are assumed, as shown in FIG. 13. In this comparative example, too, in directions parallel to the longitudinal axis C, the position where the deflecting amount of the probe 3A is always zero does not coincide with to the position of the rotation axis R of the jaw 52A. However, in this comparative example, the jaw 52A includes a jaw body 81 rotatably attached to the sheath 23A, and a wiper member 83 attached to the jaw body 81 via a pin 82. The wiper member 83 is rotatable relative to the jaw body 81 around the pin 82. This configuration allows the probe facing portion 55 of the jaw 52A to abut on the jaw facing portion 58 of the probe 3A without any clearance therebetween even when the jaw 52A is in abutment with the first electrode portion 21 of the probe 3A and the part of the probe 3A provided to the distal direction side of the most-distal support member 51A deflects. The above-described configurations of the probe 3A, the sheath 23A, and the jaw 52A are also used in the ultrasonic coagulation-and-cutting device according to Jpn. Pat. Appln. KOKAI Publication No. 2009-261911.

However, in this comparative example, the jaw body 81 is coupled to the wiper member 83 by the pin 82, so that number of components is increased, and the assembly of the jaw is more complicated. Moreover, as the jaw body 81 is coupled to the wiper member 83 by the pin 82, the conduction of heat between the jaw body 81 and the wiper member 83 deteriorates. According to the present embodiment, frictional heat is generated by the ultrasonic vibrations and heat is generated by the high-frequency current when ultrasonic energy and high-frequency energy are used as the energy. It is therefore necessary to conduct the generated heat to the proximal direction side and prevent, for example, deformation of the first electrode portion 21 and the jaw 52A resulting from thermal expansion. According to the first comparative example, the conduction of heat from the jaw 52A toward the proximal direction side deteriorates due to the deterioration of the conduction of heat between the jaw body 81 and the wiper member 83. As a result, the jaw 52A is deformed by thermal expansion, and the performance of grasping the living tissue between the jaw 52A and the first electrode portion 21 of the probe 3A deteriorates.

Thus, according to the present embodiment, in the directions parallel to the longitudinal axis C, the position where the deflecting amount of the probe 3 is always zero coincides with the position of the rotation axis R of the jaw 52, as shown in FIG. 8. Therefore, when the jaw 52 is in abutment with the first electrode portion 21 of the probe 3 (the distal portion of the probe 3) and the part of the probe 3 provided to the distal direction side of the most-distal support member 51A deflects, the probe facing portion 55 of the jaw 52 abuts on the jaw facing portion 58 of the probe 3 with no space therebetween. Consequently, the living tissue is efficiently treated (cut) between the first electrode portion 21 and the second electrode portion 53 by energy such as ultrasonic vibrations. In contrast with the jaw 52A, the jaw 52 is not provided with the wiper member 83. Therefore, the heat generated when the living tissue is treated is efficiently conducted to the proximal direction side.

As a second comparative example, a probe 3B, a sheath 23B, and a jaw 52B are assumed, as shown in FIG. 14. In this comparative example, in directions parallel to the longitudinal axis C, the position of the rotation axis R of the jaw 52B coincides with the position of the most-distal support member 51A, as in the first embodiment. Thus, in the directions parallel to the longitudinal axis C, the position where the deflecting amount of the probe 3 is always zero coincides with the position of the rotation axis R of the jaw 52B. However, in this comparative example, the probe facing portion 55 of the jaw 52B is parallel to the jaw facing portion 58 of the probe 3B when in abutment with the first electrode portion 21 of the probe 3, in contrast with the first embodiment. That is, when the probe facing portion 55 of the jaw 52B is parallel to the jaw facing portion 58 of the probe 3B, there is no clearance between the probe facing portion 55 and the jaw facing portion 58.

Owing to such a configuration, in this comparative example, a proximal part of the probe facing portion 55 of the jaw 52B first contacts a living tissue S when the living tissue S is grasped between the first electrode portion 21 of the probe 3B and the second electrode portion 53 of the jaw 52B, as shown in FIG. 15. Therefore, during the treatment of the living tissue S, a distal part of the probe facing portion 55 of the jaw 52B may not be in contact with the living tissue S.

Thus, as shown in FIG. 9 according to the present embodiment, when the jaw 52 closes relative to the first electrode portion 21, the probe facing portion 55 of the jaw 52 is preferably parallel to the jaw facing portion 58 of the probe 3 with the predetermined distance D therebetween before abutting on the first electrode portion 21 of the probe 3. That is, when the probe facing portion 55 of the jaw 52 is parallel to the jaw facing portion 58 of the probe 3, the probe facing portion 55 is preferably separate from the jaw facing portion 58 at the predetermined distance D.

According to this configuration, a distal part of the probe facing portion 55 of the jaw 52 first contacts the living tissue S when the living tissue S, for example, a blood vessel is grasped between the first electrode portion 21 of the probe 3 and the second electrode portion 53 of the jaw 52, as shown in FIG. 16. Therefore, during the treatment of the living tissue S, the whole probe facing portion 55 of the jaw 52 is in contact with the living tissue S. As a result, a force is uniformly applied to the living tissue S grasped between the first electrode portion 21 of the probe 3 (the distal portion of the probe 3) and the second electrode portion 53 (the jaw 52). Consequently, the living tissue S is more efficiently treated between the first electrode portion 21 and the second electrode portion 53 by using energy (ultrasonic vibrations).

A foot switch has heretofore been used in the input operation to, for example, generate ultrasonic vibrations and supply a high-frequency current. However, as the operator does not see his/her feet during a treatment, it is difficult for the operator to recognize the position of the foot switch. Thus, working efficiency at the time of the treatment deteriorates when the input operation is performed with the foot switch.

Accordingly, in the ultrasonic coagulation-and-cutting device according to Jpn. Pat. Appln. KOKAI Publication No. 2009-261911, an input button configured to perform the input operation is provided in the fixed handle. However, in this ultrasonic coagulation-and-cutting device, the fixed handle extends in a direction out of the longitudinal axis. A movable handle is configured to open/close relative to the fixed handle in directions substantially parallel to the longitudinal axis. In contrast, according to the present embodiment, the movable handle 25 is configured to open/close relative to the fixed handle 22 in the first open/close direction (direction indicated by the arrow A1 in FIG. 1) perpendicular to the longitudinal axis C and in the second open/close direction (direction indicated by the arrow A2 in FIG. 1) opposite to the first open/close direction. The movable handle 25 is located to the first open/close direction side of the fixed handle 22.

When the movable handle 25 is configured to open/close in the first open/close direction and the second open/close direction that are perpendicular to the longitudinal axis C as in the present embodiment, the positions of the input buttons 35A and 35B are restricted. That is, the input buttons 35A and 35B need to be provided in a part of the fixed handle 22, extending along the longitudinal axis C, which is located on the second open/close direction side and provided to the distal direction side of the fixed handle ring 28.

Here, as a third comparative example, a fixed handle 22C is assumed, as shown in FIG. 17. As shown in FIG. 17, the fixed handle 22C extends along the longitudinal axis C as the fixed handle 22 according to the present embodiment. The input buttons 35A and 35B are provided in the part of the fixed handle 22C located on the second open/close direction side and provided to the distal direction side of the fixed handle ring 28. The axis L1 of the movable handle 25 is inclined at the acute angle α to the longitudinal axis C. However, in contrast with the fixed handle 22, the fixed handle 22C is not provided with the inclined plane 33. In the fixed handle 22C, the press direction of the input buttons 35A and 35B is same as one of diametrical directions of the fixed handle 22C. That is, the press direction of the input buttons 35A and 35B is perpendicular to the longitudinal axis C. When the input buttons 35A and 35B are pressed in a direction perpendicular to the longitudinal axis C, the sheath unit 4 and the probe 3 including the fixed handle 22C are more easily vibrated perpendicular to the longitudinal axis C by the press force. Thus, the positions of the distal portion of the probe 3 and the jaw 52 are not easily fixed during a treatment, and working efficiency at the time of the treatment deteriorates.

Accordingly, as a fourth comparative example, a fixed handle 22D is assumed, as shown in FIG. 18. As shown in FIG. 18, the fixed handle 22D is similar in configuration to the fixed handle 22C according to the third comparative example except that the press direction of the input buttons 35A and 35B is different. The press direction of the input buttons 35A and 35B is parallel to the longitudinal axis C. In this comparative example, as the input buttons 35A and 35B are pressed parallel to the longitudinal axis C, the sheath unit 4 and the probe 3 including the fixed handle 22D are not easily vibrated perpendicular to the longitudinal axis C by the press force. The above-described configurations of the input buttons 35A and 35B that are pressed parallel to the longitudinal axis C are also used in the ultrasonic treatment device shown in Jpn. PCT National Publication No. 2009-514566.

However, as described above, when the fixed handle 22D and the movable handle 25 are grasped, the fore finger F2 and the middle finger F3 extend at a slant relative to the longitudinal axis C. That is, the extending directions of the fore finger F2 and the middle finger F3 are at the slant relative to the longitudinal axis C. When the fixed handle 22D and the movable handle 25 are grasped, the input operation is performed with the fore finger F2 in the input buttons 35A and 35B. In this comparative example, the press direction of the input buttons 35A and 35B is parallel to the longitudinal axis C. Thus, the extending direction of the fore finger F2 is not parallel to the press direction of the input buttons 35A and 35B. Therefore, when the fixed handle 22D and the movable handle 25 are grasped, it is difficult to press the input buttons 35A and 35B. As a result, when the fixed handle 22D and the movable handle 25 are grasped, operability of the input buttons 35A and 35B, which are the operation input sections, deteriorates.

In contrast, according to the present embodiment, the inclined plane 33, inclined relative to the longitudinal axis C, is provided in the part of the handle casing 27 (fixed handle 22) located on the second open/close direction side. The inclined plane 33 is an ascending slope as it goes from the distal direction toward the proximal direction in the handle casing 27. The inclined plane 33 is provided to the distal direction side of the fixed handle ring 28. The input buttons 35A and 35B, which are two operation input sections, are provided in the inclined plane 33. The press direction of the input buttons 35A and 35B is perpendicular to the inclined plane 33. As described above, according to the present embodiment, the press direction of the input buttons 35A and 35B is not perpendicular to the longitudinal axis C. Therefore, the sheath unit 4 and the probe 3 including the fixed handle 22D are not easily vibrated perpendicular to the longitudinal axis C by the press force. Thus, the positions of the distal portion of the probe 3 and the jaw 52 are easily fixed during a treatment.

Such a configuration allows the extending direction of the fore finger F2 to be substantially perpendicular to the inclined plane 33. That is, the inclined plane 33 is a plane substantially perpendicular to the extending direction of the fore finger F2 in a grasping state. In other words, the extending direction of the fore finger F2 is substantially parallel to the press direction of the input buttons 35A and 35B. Therefore, the input buttons 35A and 35B can be easily pressed even when the fixed handle 22 and the movable handle 25 are grasped. As a result, an operation can be easily performed with the input buttons 35A and 35B, which are the operation input sections, when the fixed handle 22 and the movable handle 25 are grasped.

When a high-frequency current is supplied from the high-frequency current controller 9 in response to the input operation at the input buttons 35A and 35B, the high-frequency current runs through the probe side current path and the jaw side current path. In this way, a bipolar treatment by a high-frequency current is conducted by the first electrode portion 21 of the probe 3 and the second electrode portion 53 of the jaw 52. At the same time, constant transmission of the high-frequency current between the sheath 23 and the second electrode portion 53 of the jaw 52 is maintained by the electric contact unit 60 between the sheath 23 and the jaw 52 in the jaw side current path.

Here, as a fifth comparative example, an electric contact unit 60E is assumed, as shown in FIG. 19. As shown in FIG. 19, the electric contact unit 60E includes the grooves 61A and 61B that are provided in the jaw 52 to be recessed toward an outer peripheral direction along the rotation axis R, as the electric contact unit 60 according to the first embodiment. The electric contact unit 60E also includes the projections 63A and 63B that are provided in the outer peripheral portion of a sheath 23E to protrude toward the outer peripheral direction along the rotation axis R. The first projection 63A is engaged with the first groove 61A, and the second projection 63B is engaged with the second groove 61B. That is, the projections 63A and 63B are engaged with the grooves 61A and 61B without any clearance between the projections 63A and 63B and the groove defining portions 62A and 62B. Therefore, the projections 63A and 63B of the electric contact unit 60E do not include the projection side semispherical portion 75 semispherically provided to extend to the sheath side contact portion 71 along the rotation axis R.

As the projections 63A and 63B are engaged with the grooves 61A and 61B, the jaw side contact portion 73 and the sheath side contact portion 71 are always kept in contact in the electric contact unit 60E. This maintains constant transmission of the high-frequency current between the sheath 23E and the second electrode portion 53 of a jaw 52E. However, frictional resistance between the sheath 23E and the jaw 52E is increased by the engagement of the projections 63A and 63B with the grooves 61A and 61B. With the increase of the frictional resistance, a driving force necessary to open/close the jaw 52E increases, and operability at the time of the opening/closing of the jaw 52E deteriorates.

As a sixth comparative example, an electric contact unit 60F is assumed, as shown in FIG. 20. As shown in FIG. 20, the electric contact unit 60F includes the grooves 61A and 61B that are provided in a jaw 52F to be recessed toward an outer pperipheral direction along the rotation axis R, as the electric contact unit 60 according to the first embodiment. The electric contact unit 60F also includes the projections 63A and 63B that are provided in the outer peripheral portion of a sheath 23F to protrude in the outer peripheral direction along the rotation axis R. The first projection 63A is inserted in the first groove 61A, and the second projection 63B is inserted in the second groove 61B. The projections 63A and 63B are inserted in the grooves 61A and 61B with clearances provided between the projections 63A and 63B and the groove defining, portions 62A and 62B defining the grooves 61A and 61B. In this case, the groove defining portions 62A and 62B of the jaw 52F are movable relative to the projections 63A and 63B by the dimensions of the clearances. The projections 63A and 63B of the electric contact unit 60E do not include the projection side semispherical portion 75 semispherically provided along the rotation axis R.

The frictional resistance between the sheath 23F and the jaw 52F is reduced by the clearances between the projections 63A and 63B and the groove defining portions 62A and 62B. However, in such a configuration, the clearances are provided between the projections 63A and 63B and the groove defining portions 62A and 62B, so that the sheath 23F is not always in contact with the jaw 52F. Thus, a high-frequency current is not always transmitted between the sheath 23F and the jaw 52F. Therefore, the stability of the transmission of the high-frequency current between the sheath 23F and the jaw 52F deteriorates.

In contrast, according to the present embodiment, the projections 63A and 63B are inserted in the grooves 61A and 61B with clearances between the projections 63A and 63B and the groove side surfaces 65 of the groove defining portions 62A and 62B. The sheath side contact portions 71 are located in the protruding ends 69 of the projections 63A and 63B, and the jaw side contact portions 73 are located in the groove bottom surfaces 67 of the groove defining portions 62A and 62B. When the jaw 52 is not attached to the sheath 23, the first dimension T1 along the rotation axis R from the longitudinal axis C to the sheath side contact portion 71 is greater than the second dimension T2 along the rotation axis R from the longitudinal axis C to the jaw side contact portion 73. This maintains the constant contact between the jaw side contact portion 73 and the sheath side contact portion 71 even when the clearances are provided between the projections 63A and 63B and the groove side surfaces 65 of the groove defining portions 62A and 62B. Thus, transmission of a high-frequency current is maintained between the sheath 23 and the second electrode portion 53 of the jaw 52.

The projections 63A and 63B include the projection side semispherical portions 75 semispherically provided to extend to the sheath side contact portion 71 along the rotation axis R. The projection side semispherical portions 75 decrease in the sectional area perpendicular to the rotation axis R as they go toward the protruding ends 69 of the projections 63A and 63B along the rotation axis R. That is, the area of contact between the sheath side contact portion 71 and the jaw side contact portion 73 is reduced by the projection side semispherical portion 75. The frictional resistance between the sheath 23 and the jaw 52 is reduced by the reduction of the contact area between the sheath side contact portion 71 and the jaw side contact portion 73. As a result, the driving force necessary to open/close the jaw 52 decreases, and operability at the time of the opening/closing of the jaw 52 improves.

The sheath side contact portion 71 is provided in the outer peripheral portion of the sheath 23. The jaw side contact portion 73 is provided in the inner peripheral portion of the jaw 52. Thus, the sheath side contact portion 71 and the jaw side contact portion 73 are not exposed in the external surface of the sheath 23 and the external surface of the jaw 52. Therefore, the operator does not receive an electric shock even when, for example, the hand of the operator touches the external surface in the distal portion of the sheath or the external surface of the jaw. According to this configuration, an insulating coating is not needed in parts that are difficult to coat, such as the projections 63A and 63B and the groove defining portions 62A and 62B.

Accordingly, the medical treatment device 1 having the configuration described above has the following advantageous effects. That is, in the medical treatment device 1 (bipolar treatment device) according to the present embodiment, the sheath side contact portions 71 are located in the protruding ends 69 of the projections 63A and 63B, and the jaw side contact portions 73 are located in the groove bottom surfaces 67 of the groove defining portions 62A and 62B. When the jaw 52 is not attached to the sheath 23, the first dimension T1 along the rotation axis R from the longitudinal axis C to the sheath side contact portion 71 is greater than the second dimension T2 along the rotation axis R from the longitudinal axis C to the jaw side contact portion 73. This maintains the constant contact between the jaw side contact portion 73 and the sheath side contact portion 71 even when the clearances are provided between the projections 63A and 63B and the groove side surfaces 65 of the groove defining portions 62A and 62B. Thus, transmission of a high-frequency current is maintained between the sheath 23 and the second electrode portion 53 of the jaw 52. Consequently, the high-frequency current can be stably transmitted between the sheath 23 and the jaw 52.

In the medical treatment device 1 (bipolar treatment device), the projections 63A and 63B are inserted in the grooves 61A and 61B with clearances between the projections 63A and 63B and the groove side surfaces 65 of the groove defining portions 62A and 62B. The projections 63A and 63B include the projection side semispherical portions 75 semispherically provided to extend to the sheath side contact portion 71 along the rotation axis R. The projection side semispherical portions 75 are configured to decrease in the sectional area perpendicular to the rotation axis R as they go toward the protruding ends 69 of the projections 63A and 63B along the rotation axis R. That is, the area of contact between the sheath side contact portion 71 and the jaw side contact portion 73 is reduced by the projection side semispherical portion 75. The frictional resistance between the sheath 23 and the jaw 52 is reduced by the reduction of the contact area between the sheath side contact portion 71 and the jaw side contact portion 73. As a result, the driving force necessary to open/close the jaw 52 decreases, and operability at the time of the opening/closing of the jaw 52 improves.

In the medical treatment device 1 (bipolar treatment device), the sheath side contact portion 71 is provided in the outer peripheral portion of the sheath 23. The jaw side contact portion 73 is provided in the inner peripheral portion of the jaw 52. Thus, the sheath side contact portion 71 and the jaw side contact portion 73 are not exposed in the external surface of the sheath 23 and the external surface of the jaw 52. This can prevent the operator from receiving an electric shock even when, for example, the hand of the operator touches the external surface in the distal portion of the sheath 23 or the external surface of the jaw 52. According to this configuration, an insulating coating is not needed in parts that are difficult to coat with, such as the projections 63A and 63B and the groove defining portions 62A and 62B. Consequently, the medical treatment device 1 (bipolar treatment device) can be easily manufactured, the manufacturing time is reduced, and the manufacturing costs can be reduced.

In the medical treatment device 1 (grasping treatment device), in the directions parallel to the longitudinal axis C, the position of the rotation axis R of the jaw 52 coincides with the position of the most-distal support member 51A. That is, in the directions parallel to the longitudinal axis C, the position where the deflecting amount of the probe 3 is always zero coincides with the position of the rotation axis R of the jaw 52. Therefore, when the jaw 52 is in abutment with the first electrode portion 21 of the probe 3 and the part of the probe 3 provided to the distal direction side of the most-distal support member 51A deflects, the probe facing portion 55 of the jaw 52 abuts on the jaw facing portion 58 of the probe 3 with no space therebetween. Thus, during the treatment of the living tissue S, the whole probe facing portion 55 of the jaw 52 is in uniform contact with the living tissue S. As a result, a force is uniformly applied to the living tissue S grasped between the first electrode portion 21 and the second electrode portion 53. Consequently, the living tissue S can be more efficiently treated (cut) between the first electrode portion 21 (the distal portion of the probe 3) and the second electrode portion 53 (the jaw 52) by using energy such as ultrasonic vibrations. In such a configuration, the jaw 52 does not need to include the jaw body (81), and the wiper member (83) rotatably attached to the jaw body (81). That is, the jaw 52 can be integrally formed into one unit. Therefore, the heat generated when the grasping target (living tissue) is treated (cut) can be efficiently conducted to the proximal direction side.

In the medical treatment device 1 (grasping treatment device) which is an ultrasonic treatment device, the support member 51 including the most-distal support member 51A is located at the node position of ultrasonic waves. This can more effectively prevent the contact between the probe 3 and the sheath 23.

In the medical treatment device 1 (grasping treatment device), when the jaw 52 closes relative to the first electrode portion 21, the probe facing portion 55 of the jaw 52 is parallel to the jaw facing portion 58 of the probe 3 with the predetermined distance D therebetween before abutting on the first electrode portion 21 of the probe 3. That is, when the probe facing portion 55 of the jaw 52 is parallel to the jaw facing portion 58 of the probe 3, the probe facing portion 55 is separate from the jaw facing portion 58 at the predetermined distance D. According to this configuration, the distal part of the probe facing portion 55 of the jaw 52 first contacts the living tissue S when the living tissue S is grasped between the first electrode portion 21 of the probe 3 and the second electrode portion 53 of the jaw 52. Therefore, during the treatment of the living tissue S, the whole probe facing portion 55 of the jaw 52 is in uniform contact with the living tissue S. As a result, force is uniformly applied to the living tissue S grasped between the first electrode portion 21 and the second electrode portion 53. Consequently, the living tissue S can be more efficiently treated (cut) between the first electrode portion 21 (the distal portion of the probe 3) and the second electrode portion 53 (the jaw 52) by using energy such as ultrasonic vibrations.

In the medical treatment device 1, the inclined plane 33, inclined relative to the longitudinal axis C, is provided in the part of the handle casing 27 (fixed handle 22) on the second open/close direction side. The inclined plane 33 is provided to the distal direction side of the fixed handle ring 28. The input buttons 35A and 35B, which are two operation input sections, are provided in the inclined plane 33. The press direction of the input buttons 35A and 35B is perpendicular to the inclined plane 33. According to this configuration, the press direction of the input buttons 35A and 35B is not perpendicular to the longitudinal axis C. Therefore, the sheath unit 4 and the probe 3 including the fixed handle 22 are not easily vibrated perpendicular to the longitudinal axis C by the press force. Thus, the positions of the distal portion of the probe 3 and the jaw 52 can be easily fixed during a treatment.

Such a configuration allows the extending directions of the fore finger F2 and the middle finger F3 to be substantially perpendicular to the inclined plane 33 when the operator grasps the medical treatment device 1. That is, the extending direction of the fore finger F2 is substantially parallel to the press direction of the input buttons 35A and 35B. Therefore, the input buttons 35A and 35B can be easily pressed even when the fixed handle 22 and the movable handle 25 are grasped. As a result, an operation can be easily performed with the input buttons 35A and 35B that are the operation input sections when the fixed handle 22 and the movable handle 25 are grasped.

(Modifications)

Although the projections 63A and 63B include the projection side semispherical portions 75 semispherically provided to extend to the sheath side contact portion 71 along the rotation axis R according to the first embodiment, the present invention is not limited thereto. For example, as a first modification, the first projection 63A may include, instead of the projection side semispherical portion 75, a protrusion side tapered portion 77 provided in a tapered form to extend to the sheath side contact portion 71 along the rotation axis R, as shown in FIG. 21. The protrusion side tapered portion 77 is a projection side sectional changing portion which is configured to decrease in the sectional area perpendicular to the rotation axis R as it goes toward the protruding end 69 of the first projection 63A along the rotation axis R. The area of contact between the sheath side contact portion 71 and the jaw side contact portion 73 is reduced by the protrusion side tapered portion 77. The protrusion side tapered portion 77 is also provided in the second projection 63B as in the first projection 63A.

For example, as a second modification, the first projection 63A may include a protrusion side tapered portion 78 provided in a tapered form along the rotation axis R, and a columnar portion 79 provided to the protruding end 69 side of the protrusion side tapered portion 78 to extend to the sheath side contact portion 71 along the rotation axis R, as shown in FIG. 22. The protrusion side tapered portion 78 is a projection side sectional changing portion which is configured to decrease in the sectional area perpendicular to the rotation axis R as it goes toward the protruding end 69 of the first projection 63A along the rotation axis R. In the columnar portion 79, the area of its section perpendicular to the rotation axis R is constant. According to this modification, the area of contact between the sheath side contact portion 71 and the jaw side contact portion 73 is reduced by the protrusion side tapered portion 78. The protrusion side tapered portion 78 is also provided in the second projection 63B as in the first projection 63A.

As described above, according to the first embodiment, the first modification, and the second modification, the grooves 61A and 61B, which are provided in the jaw 52 to be recessed toward the outer peripheral direction along the rotation axis R, are defined by the groove defining portions 62A and 62B. The jaw side contact portions 73 are located in the groove bottom surfaces 67 of the groove defining portions 62A and 62B. The projections 63A and 63B are provided in the outer peripheral portion of the sheath 23 to protrude toward the outer peripheral direction along the rotation axis R. The projections 63A and 63B are inserted in the grooves 61A and 61B. The sheath side contact portions 71 are located in the protruding ends 69 of the projections 63A and 63B. Each of the projections 63A and 63B includes a projection side sectional changing portion (75, 77, 78) which is configured to decrease in the sectional area perpendicular to the rotation axis R as it goes toward the protruding end 69 along the rotation axis R. The area of contact between the sheath side contact portion 71 and the jaw side contact portion 73 is reduced by the projection side sectional changing portion (75, 77, 78).

No projection side sectional changing portion (75, 77, 78) may be provided. For example, as a third modification, the first groove defining portion 62A may include a convex portion 85 which defines the groove bottom surface 67 so that the jaw side contact portion 73 protrudes toward the protruding end 69 of the first projection 63A, as shown in FIG. 23. According to this modification, when the jaw 52 is not attached to the sheath 23, the first dimension T1 along the rotation axis R from the longitudinal axis C to the sheath side contact portion 71 is greater than the second dimension T2 along the rotation axis R from the longitudinal axis C to the jaw side contact portion 73, as in the first embodiment. This maintains the constant contact between the jaw side contact portion 73 and the sheath side contact portion 71 even when a clearance is provided between the first projection 63A and the groove side surface 65 of the first groove defining portion 62A. The convex portion 85 is also provided in the second groove defining portion 62B as in the first groove defining portion 62A.

According to this modification, no projection side sectional changing portion (75, 77, 78) is provided. Instead, the convex portion 85 of each of the groove defining portions 62A and 62B includes a groove side semispherical portion 87 semispherically provided to extend to the jaw side contact portion 73 along the rotation axis R. The groove side semispherical portion 87 is a groove side sectional changing portion which is configured to decrease in the sectional area perpendicular to the rotation axis R as it goes toward the jaw side contact portion 73 along the rotation axis R. The area of contact between the sheath side contact portion 71 and the jaw side contact portion 73 is reduced by the groove side semispherical portion 87.

The groove side sectional changing portion is the groove side semispherical portion 87 according to this modification, but is not limited thereto. For example, the groove side sectional changing portion (87) may be provided in a tapered form to extend to the jaw side contact portion 73 along the rotation axis R. The groove side sectional changing portion (87) does not need to extend to the jaw side contact portion 73. That is, the groove side sectional changing portion (87) has only to decrease in the sectional area perpendicular to the rotation axis R as it goes toward the jaw side contact portion 73 along the rotation axis R.

As described above, according to the third modification, the grooves 61A and 61B, which are provided in the jaw 52 to be recessed toward the outer peripheral direction along the rotation axis R, are defined by the groove defining portions 62A and 62B. The jaw side contact portions 73 are located in the groove bottom surfaces 67 of the groove defining portions 62A and 62B. The projections 63A and 63B are provided in the outer peripheral portion of the sheath 23 to protrude toward the outer peripheral direction along the rotation axis R. The projections 63A and 63B are inserted in the grooves 61A and 61B. The sheath side contact portions 71 are located in the protruding ends 69 of the projections 63A and 63B. Each of the groove defining portions 62A and 62B includes the convex portion 85, which defines the groove bottom surface 67 so that the jaw side contact portion 73 protrudes toward the protruding end 69 of each of the projections 63A and 63B. The projecting portion 85 includes the groove side sectional changing portion (87) which is configured to decrease in the sectional area perpendicular to the rotation axis R as it goes toward the jaw side contact portion 73 along the rotation axis R. The area of contact between the sheath side contact portion 71 and the jaw side contact portion 73 is reduced by the groove side sectional changing portion (87).

Although the projection side sectional changing portion (75, 77, 78) or the groove side sectional changing portion (87) is provided according to the first embodiment, the first modification, the second modification, and the third modification, the present invention is not limited thereto. For example, both the projection side sectional changing portion (75, 77, 78) and the groove side sectional changing portion (87) may be provided. That is, at least one of the projection side sectional changing portion (75, 77, 78) and the groove side sectional changing portion (87) has only to be provided.

According to the first embodiment, the grooves 61A and 61B, which are recessed toward the outer peripheral direction, are provided in the jaw 52, and the projections 63A and 63B, which protrude toward the outer peripheral direction, are provided in the sheath 23. However, the present invention is not limited thereto. For example, as a fourth modification, the electric contact unit 60 may be provided with no grooves 61A and 61B and no projections 63A and 63B, as shown in FIG. 24. According to this modification, the electric contact unit 60 is provided with a first groove 91A and a second groove 91B which are provided in the outer peripheral portion of the sheath 23 to be recessed toward an inner peripheral direction along the rotation axis R. The first groove 91A is recessed toward the first rotation axis direction (direction indicated by the arrow B1 in FIG. 24) parallel to the rotation axis R. The second groove 91B is recessed toward the second rotation axis direction (direction indicated by the arrow B2 in FIG. 24) opposite to the first rotation axis direction. The first groove 91A is defined by a first groove defining portion 92A, and the second groove 91B is defined by a second groove defining portion 92B.

In the electric contact unit 60, a first projection 93A and a second projection 93B which protrude toward the inner peripheral direction along the rotation axis R are also provided in the jaw 52. The first projection 93A protrudes toward the first rotation axis direction, and the second projection 93B protrudes toward the second rotation axis direction. The first projection 93A is inserted in the first groove 91A, and the second projection 93B is inserted in the second groove 91B.

FIG. 25 is a diagram showing the configurations of the first groove defining portion 92A and the first projection 93A. Although only the first groove defining portion 92A and the first projection 93A are described below, the second groove defining portion 92B is similar in configuration to the first groove defining portion 92A, and the second projection 93B is similar in configuration to the first projection 93A. Therefore, the second groove defining portion 92B and the second projection 93B are not described.

As shown in FIG. 25, the first groove defining portion 92A includes a groove side surface 95 and a groove bottom surface 97. The first projection 93A includes a protruding end 99. The first projection 93A is inserted in the first groove 91A with a clearance between the first projection 93A and the groove side surface 95. The jaw side contact portion 73 is located in the protruding end 99. That is, the jaw side contact portion 73 is provided in the inner peripheral portion of the jaw 52. The sheath side contact portion 71 is located in the groove bottom surface 97 of the first groove defining portion 92A of the sheath 23. That is, the sheath side contact portion 71 is provided in the outer peripheral portion of the sheath 23. The jaw side contact portion 73 slidably contacts the sheath side contact portion 71. When the jaw side contact portion 73 contacts the sheath side contact portion 71, a high-frequency current is transmitted between the sheath 23 and the second electrode portion 53 of the jaw 52.

Figure 26:
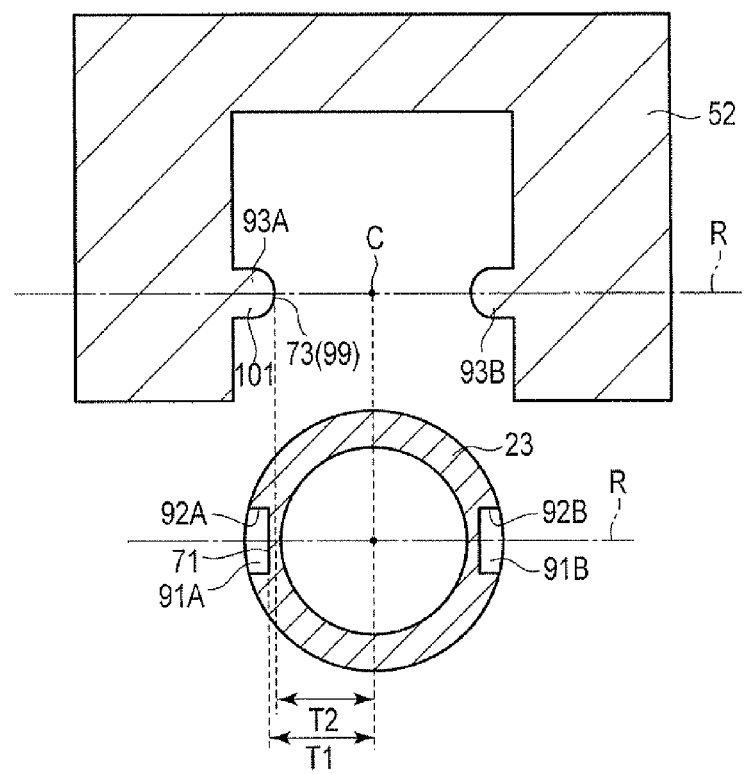
FIG. 26 is a schematic sectional view showing the sheath and the jaw when the jaw is not attached to the sheath according to the fourth modification.

FIG. 26 is a diagram showing the sheath 23 and the jaw 52 when the jaw 52 is not attached to the sheath 23. As shown in FIG. 26, when the jaw 52 is not attached to the sheath 23, the first dimension T1 along the rotation axis R from the longitudinal axis C to the sheath side contact portion 71 is greater than the second dimension T2 along the rotation axis R from the longitudinal axis C to the jaw side contact portion 73. This configuration maintains the constant contact between the jaw side contact portion 73 and the sheath side contact portion 71 even when a clearance is provided between the first projection 93A and the groove side surface 95 of the first groove defining portion 92A. Thus, transmission of a high-frequency current is maintained between the sheath 23 and the second electrode portion 53 of the jaw 52.

As shown in FIG. 25, the first projection 93A includes a projection side semispherical portion 101 semispherically provided to extend to the jaw side contact portion 73 along the rotation axis R. The projection side semispherical portion 101 is a projection side sectional changing portion which is configured to decrease in the sectional area perpendicular to the rotation axis R as it goes toward the protruding end 99 of the first projection 93A along the rotation axis R. The area of contact between the sheath side contact portion 71 and the jaw side contact portion 73 is reduced by the projection side semispherical portion 101.

The projection side sectional changing portion is the projection side semispherical portion 101 according to this modification, but is not limited thereto. For example, the projection side sectional changing portion (101) may be provided in a tapered form to extend to the jaw side contact portion 73 along the rotation axis R. The projection side sectional changing portion (101) does not need to extend to the jaw side contact portion 73. That is, the projection side sectional changing portion (101) has only to decrease in the sectional area perpendicular to the rotation axis R as it goes toward the jaw side contact portion 73 (protruding end 99) along the rotation axis R.

As described above, according to the fourth modification, the grooves 91A and 91B, which are provided in the outer peripheral portion of the sheath 23 to be recessed toward the inner peripheral direction along the rotation axis R, are defined by the groove defining portions 92A and 92B. The sheath side contact portions 71 are located in the groove bottom surfaces 97 of the groove defining portions 92A and 92B. The projections 93A and 93B are provided in the jaw 52 to protrude toward the inner peripheral direction along the rotation axis R. The projections 93A and 93B are inserted in the grooves 91A and 91B. The jaw side contact portions 73 are located in the protruding ends 99 of the projections 93A and 93B. Each of the projections 93A and 93B includes the projection side sectional changing portion (101) which is configured to decrease in the sectional area perpendicular to the rotation axis R as it goes toward the protruding end 99 along the rotation axis R. The area of contact between the sheath side contact portion 71 and the jaw side contact portion 73 is reduced by the projection side sectional changing portion (101).

Figure 27A:
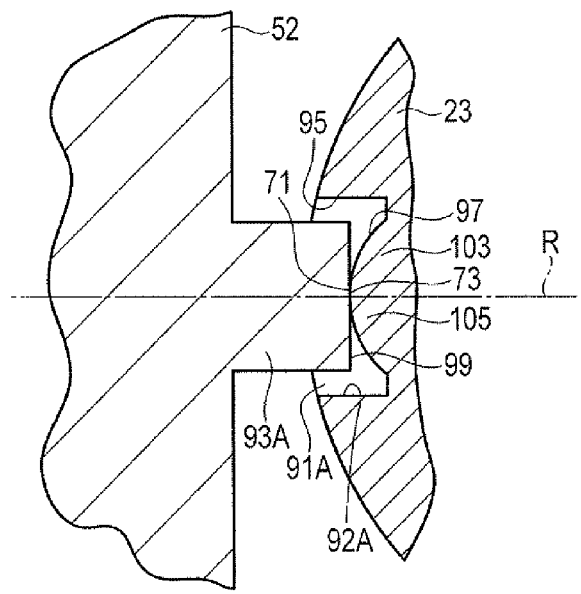
FIG. 27A is a schematic sectional view showing the configurations of the first groove defining portion and the first projection of the electric contact unit according to a fifth modification.

No projection side sectional changing portion (101) may be provided. For example, as a fifth modification, the first groove defining portion 92A may include a convex portion 103 which defines the groove bottom surface 97 so that the sheath side contact portion 71 protrudes toward the protruding end 99 of the first projection 93A, as shown in FIG. 27A. According to this modification again, when the jaw 52 is not attached to the sheath 23, the first dimension T1 along the rotation axis R from the longitudinal axis C to the sheath side contact portion 71 is greater than the second dimension T2 along the rotation axis R from the longitudinal axis C to the jaw side contact portion 73, as in the fourth modification. This maintains the constant contact between the jaw side contact portion 73 and the sheath side contact portion 71 even when a clearance is provided between the first projection 93A and the groove side surface 95 of the first groove defining portion 92A. The convex portion 103 is also provided in the second groove defining portion 92B as in the first groove defining portion 92A.

According to this modification, no projection side sectional changing portion (101) is provided. Instead, the convex portion 103 of each of the groove defining portions 92A and 92B includes a groove side semispherical portion 105 semispherically provided to extend to the sheath side contact portion 71 along the rotation axis R. The groove side semispherical portion 105 is a groove side sectional changing portion which is configured to decrease in the sectional area perpendicular to the rotation axis R as it goes toward the sheath side contact portion 71 along the rotation axis R. The area of contact between the sheath side contact portion 71 and the jaw side contact portion 73 is reduced by the groove side semispherical portion 105.

The groove side sectional changing portion is the groove side semispherical portion 105 according to this modification, but is not limited thereto. For example, the groove side sectional changing portion (105) may be provided in a tapered form to extend to the sheath side contact portion 71 along the rotation axis R. The groove side sectional changing portion (105) does not need to extend to the sheath side contact portion 71. That is, the groove side sectional changing portion (105) has only to decrease in the sectional area perpendicular to the rotation axis R as it goes toward the sheath side contact portion 71 along the rotation axis R.

As described above, according to the fifth modification, the grooves 91A and 91B, which are provided in the outer peripheral portion of the sheath 23 to be recessed toward the inner peripheral direction along the rotation axis R, are defined by the groove defining portions 92A and 92B. The sheath side contact portions 71 are located in the groove bottom surfaces 97 of the groove defining portions 92A and 92B. The projections 93A and 93B are provided in the jaw 52 to protrude toward the inner peripheral direction along the rotation axis R. The projections 93A and 93B are inserted in the grooves 91A and 91B. The jaw side contact portions 73 are located in the protruding ends 99 of the projections 93A and 93B. Each of the groove defining portions 92A and 92B includes the convex portion 103 which defines the groove bottom surface 97 so that the sheath side contact portion 71 protrudes toward the protruding end 99 of each of the projections 93A and 93B. The convex portion 103 includes the groove side sectional changing portion (105) which is configured to decrease in the sectional area perpendicular to the rotation axis R as it goes toward the sheath side contact portion 71 along the rotation axis R. The area of contact between the sheath side contact portion 71 and the jaw side contact portion 73 is reduced by the groove side sectional changing portion (105).

Although the projection side sectional changing portion (101) or the groove side sectional changing portion (105) is provided according to the fourth modification and the fifth modification, the present invention is not limited thereto. For example, both the projection side sectional changing portion (101) and the groove side sectional changing portion (105) may be provided. That is, at least one of the projection side sectional changing portion (101) and the groove side sectional changing portion (105) has only to be provided.

According to the first embodiment, the jaw 52 is directly attached to the sheath 23, and no coupling pin or the like is provided to couple the jaw 52 to the sheath 23. However, the configuration in which in the directions parallel to the longitudinal axis C, the position where the deflecting amount of the probe 3 is always zero coincides with the position of the rotation axis R of the jaw 52 is also applicable when the jaw 52 is attached to the sheath 23 via the coupling pin. That is, even when the jaw 52 rotates relative to the sheath 23 around the coupling pin (rotation axis R), the configuration in which in the directions parallel to the longitudinal axis C, the position where the deflecting amount of the probe 3 is always zero coincides with the position of the rotation axis R of the jaw 52 is available.

Although one inclined plane 33 is provided in the part of the handle casing 27 (fixed handle 22) located on the second open/close direction side according to the first embodiment, the present invention is not limited thereto. For example, as a sixth modification, a first inclined plane 33A and a second inclined plane 33B may be provided in the part of the fixed handle 22 located on the second open/close direction (direction indicated by the arrow A2 in FIG. 27B) side, as shown in FIG. 27B. In the first inclined plane 33A and the second inclined plane 33B, they go toward the proximal direction side as they go from the first open/close direction (direction indicated by the arrow A2 in FIG. 27B) toward the second open/close direction. The first inclined plane 33A and the second inclined plane 33B are provided to the distal direction side of the fixed handle ring 28. The second inclined plane 33B is located to the proximal direction side of the first inclined plane 33A.

Here, an acute first angle $\beta_1$ between the first inclined plane 33A and the longitudinal axis C is different from an acute second angle $\beta_2$ between the second inclined plane 33B and the longitudinal axis C. The first angle $\beta_1$ is greater than second angle $\beta_2$. The first angle $\beta_1$ is preferably 60° to 70°, particularly preferably 65°. The second angle $\beta_2$ is preferably 40° to 50°, particularly preferably 45°.

The first input button (first operation input section) 35A, which is one of the two operation input sections, is provided in the first inclined plane 33A, and the second input button (second operation input section) 35B, which is the other operation input section, is provided in the second inclined plane 33B. The press direction of the first input button 35A is perpendicular to the first inclined plane 33A. The press direction of the second input button 35B is perpendicular to the second inclined plane 33B.

As has been described above in the first embodiment, the input operation in the input buttons 35A and 35B is performed with the fore finger F2 when the fixed handle 22 and the movable handle 25 are grasped. Therefore, as the inclined planes 33A and 33B are provided, the extending direction of the fore finger F2 is substantially perpendicular to the inclined planes 33A and 33B when the fixed handle 22 and the movable handle 25 are grasped. That is, the extending direction of the fore finger F2 is substantially parallel to the press direction of the input buttons 35A and 35B. Therefore, the input buttons 35A and 35B can be easily pressed even when the fixed handle 22 and the movable handle 25 are grasped.

Here, the extending direction of the fore finger F2 varies between a condition in which the first input button 35A is pressed and a condition in which the second input button 35B is pressed. Thus, according to this modification, the first input button 35A is provided in the first inclined plane 33A which makes the acute first angle $\beta_1$ with the longitudinal axis C, and the second input button 35B is provided in the second inclined plane 33B which makes an acute angle smaller than the first angle $\beta_1$ with the longitudinal axis C. That is, the second inclined plane 33B, located to the proximal direction side of the first inclined plane 33A, makes a smaller acute angle with the longitudinal axis C than the first inclined plane 33A. The press direction of the first input button 35A is perpendicular to the first inclined plane 33A, and the press direction of the second input button 35B is perpendicular to the second inclined plane 33B.

Thus, when the first input button 35A is pressed with the fore finger F2 while the fixed handle 22 and the movable handle 25 are grasped, the press direction of the first input button 35A is substantially parallel to the extending direction of the fore finger F2. When the second input button 35B is pressed with the fore finger F2 while the fixed handle 22 and the movable handle 25 are grasped, the press direction of the second input button 35B is substantially parallel to the extending direction of the fore finger F2. Therefore, the extending direction of the fore finger F2 is variable between a condition in which the first input button 35A is pressed and a condition in which the second input button 35B is pressed. The input buttons 35A and 35B can be more easily pressed when the fixed handle 22 and the movable handle 25 are grasped. Consequently, when the fixed handle 22 and the movable handle 25 are grasped, an operation can be more easily performed with the input buttons 35A and 35B that are the operation input sections.

Referential Examples

FIG. 28 is a diagram showing a medical treatment device 110 according to a first referential example. As shown in FIG. 28, the medical treatment device 110 includes a vibrator unit 112, a probe 113, a sheath unit 114, and a handle unit 115. The vibrator unit 112 is similar in configuration to the vibrator unit 2 according to the first embodiment, and configured to generate ultrasonic vibrations. The probe 113 is similar in configuration to the probe 3 according to the first embodiment, and configured to transmit the ultrasonic vibrations from a proximal end to a distal end.

The sheath unit 114 includes a sheath 116 through which the probe 113 is inserted, and a jaw 117 attached to a distal portion of the sheath 116. The jaw 117 is rotatable relative to the sheath 116 via a coupling pin 118. The jaw 117 rotates relative to the sheath 116 around the rotation axis R (coupling pin 118), and the jaw 117 thereby opens/closes relative to a distal portion of the probe 113. The handle unit 115 includes a cylindrical case 121, a fixed handle 122 provided integrally with the cylindrical case 121, and a movable handle 123 configured to open/close relative to the fixed handle 122. In contrast with the first embodiment, the movable handle 123 opens/closes relative to the fixed handle 122 substantially parallel to the longitudinal axis C.

The medical treatment device 110 is configured to grasp a living tissue between the distal portion of the probe 113 and the jaw 117, as in the first embodiment. The living tissue is then cut by ultrasonic vibrations. A bipolar treatment by a high-frequency current is also performed by using the distal portion of the probe 113 and the jaw 117 as electrodes.

FIG. 29 is a diagram showing the configurations of the probe 113 and the sheath unit 114. As shown in FIG. 29, the sheath 116 includes an outer pipe 125 and an inner pipe 126. A movable member 127 is provided between the outer pipe 125 and the inner pipe 126. The jaw 117 is attached to a distal portion of the outer pipe 125 via the coupling pin 118. A distal end of the movable member 127 is connected to the jaw 117 via a connection pin 129. The movable handle 123 is coupled to the movable member 127 of the sheath 116 via an intermediary member (not shown). The movable handle 123 is opened/closed relative to the fixed handle 122, and the movable member 127 thereby moves along the longitudinal axis C. As the movable member 127 moves along the longitudinal axis C, the jaw 117 rotates relative to the sheath 116 around the rotation axis R (coupling pin 118). Thus, the jaw 117 opens/closes relative to the distal portion of the probe 113.

FIG. 30 is a diagram showing the configuration of the jaw 117. As shown in FIG. 30, the jaw 117 includes a metal jaw body 131, and an elastic member 132 attached to the jaw body 131. FIG. 31A is a diagram showing the configuration of the jaw body 131. As shown in FIG. 30 and FIG. 31A, the jaw body 131 includes a groove 133 along an axis L2 of the jaw 117. A wide portion 135 is formed in the groove 133, and is greater in a dimension in width directions (directions indicated by an arrow E2 in FIG. 30 and FIG. 31A) perpendicular to the axis L2 and perpendicular to open/close directions (directions indicated by the arrow E1 in FIG. 30 and FIG. 31A) of the jaw 117. Here, the dimension of the wide portion 135 in the width directions is U1. The dimension of parts of the groove 133 other than the wide portion 135 in the width directions is U2. A through-hole 138 which passes through the jaw body 131 in the width directions is formed in the jaw body 131. The through-hole 138 is in communication with the groove 133 at a position located to the distal direction side of the wide portion 135.

FIG. 31B is a diagram showing the configuration of the elastic member 132. As shown in FIG. 31B, the elastic member 132 includes a protrusion 136 protruding towards the width directions (directions indicated by the arrow E2 in FIG. 31B). A dimension of a part of the elastic member 132 in the width directions, in which the protrusion 136 is located in directions parallel to the axis L2, is U3. The dimension U3 is smaller than the dimension U1, and greater than the dimension U2. Here, the width directions are directions perpendicular to the axis L2 of the jaw 117 and perpendicular to the open/close directions (direction indicated by the arrow E1 in FIG. 31B) of the jaw 117. The protrusion 136 is not provided over the entire length of the elastic member 132 in the open/close directions of the jaw 117. That is, the protrusion 136 is only provided over a given dimensional range from an end of the elastic member 132 opposite to the probe 113 side toward the probe 113 side.

When the elastic member 132 is attached to the jaw body 131, the elastic member 132 is inserted into the groove 133 of the jaw body 131. In this case, the protrusion 136 is located in the wide portion 135 in the directions parallel to the axis L2. The elastic member 132 is then moved relative to the jaw body 131 toward the distal direction along the axis L2. In response to the movement of the elastic member 132, the protrusion 136 moves to a part of the groove 133 that is in communication with the through-hole 138. The protrusion 136 is then inserted into the through-hole 138. In the through-hole 138, a side surface of the protrusion 136 contacts the jaw body 131 with no clearance. This prevents the protrusion 136 from coming off the through-hole 138. As a result, the removal of the elastic member 132 from the groove 133 is prevented, and the elastic member 132 is firmly fixed to the groove 133. The jaw body 131 is then coupled to the elastic member 132 via a connection pin 137.

As shown in FIG. 29, a probe protecting member 141 is attached to an inner peripheral portion of the distal portion of the sheath 116. The probe protecting member 141 is made of an insulating material. The probe protecting member 141 is provided to have a clearance between the probe protecting member 141 and the probe 113. The contact between the probe 113 and the sheath 116 is prevented by the probe protecting member 141. The probe protecting member 141 is configured to keep the insulation between the probe 113 and the sheath 116.

FIG. 32 is a diagram showing the configuration of the probe protecting member 141. FIG. 33 is a sectional view taken along the line 33-33 of FIG. 29. As shown in FIG. 32 and FIG. 33, the probe protecting member 141 includes a groove 142 recessed toward the inner peripheral direction. The coupling pin 118, which couples the sheath 116 to the jaw 117, is provided to protrude from an inner peripheral portion of the sheath 116 toward the inner peripheral direction through the jaw 117 and the sheath 116. The coupling pin 118 is engaged with the groove 142 to attach the probe protecting member 141 to the sheath 116. The probe protecting member 141 is attached to be positioned in the directions parallel to the longitudinal axis C. When the probe protecting member 141 is positioned in the directions parallel to the longitudinal axis C, the contact between the probe 113 and the probe protecting member 141 is effectively prevented.

As shown in FIG. 29, a support member 145, which is configured to support the probe 113, is provided in the outer peripheral portion of the probe 113. The support member 145 is located at the node position of ultrasonic waves. This more effectively prevents the contact between the probe 113 and the sheath 116 (inner pipe 126). The support member 145 is configured to prevent the deflecting of the probe 113. One or more support members 145 may be provided, and at least one support member 145 has only to be provided.

Figure 34:
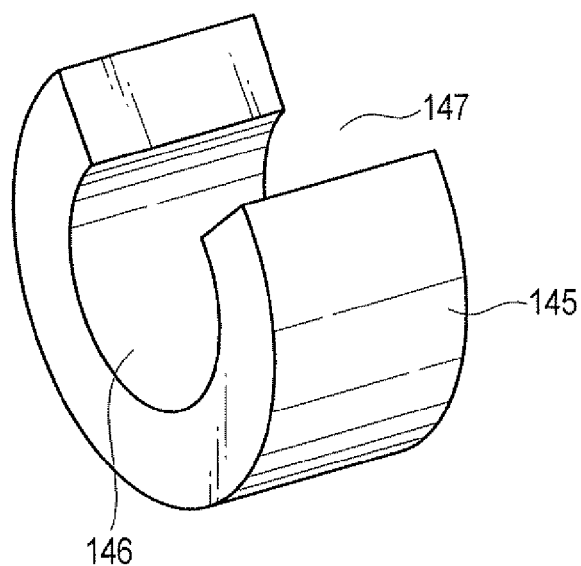
FIG. 34 is a schematic perspective view showing the configuration of a support member according to the first referential example.

FIG. 34 is a diagram showing the configuration of the support member 145. As shown in FIG. 34, the support member 145 is made of a material softer than the probe 113 and is substantially C-shaped. The support member 145 includes a groove 146 and an opening 147. When the support member 145 is attached to the outer peripheral portion of the probe 113, the probe 113 is inserted into the groove 146 of the support member 145 from the opening 147. As a result, the support member 145 is attached to the outer peripheral portion of the probe 113. an inside diameter of the support member 145 is smaller than an outside diameter of the probe 113. Therefore, when the support member 145 is attached to the outer peripheral portion of the probe 113, the support member 145 is firmly fixed to the probe 113. The support member 145 is attached to the probe 113 as described above, so that the support member 145 is more easily attached to the probe 113 than when the support member 145 is formed integrally with the probe 113, for example, by providing a rubber lining in the outer peripheral portion of the probe 113.

Figure 35:
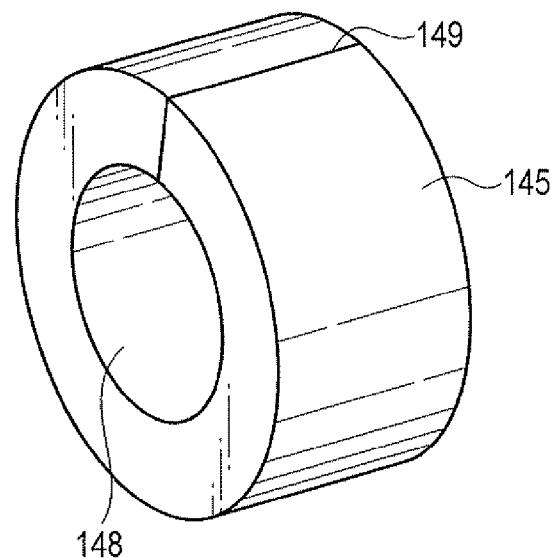
FIG. 35 is a schematic perspective view showing the configuration of the support member according to a second referential example.

The support member 145 does not need to be substantially C-shaped. For example, as a second referential example, the support member 145 may be in a substantially cylindrical shape as shown in FIG. 35. In this case, a cavity 148 is formed inside the support member 145. A cutting portion 149 is provided from the outer peripheral portion to the cavity 148. When the support member 145 is attached to the outer peripheral portion of the probe 113, the probe 113 is inserted into the cavity 148 of the support member 145 from the cutting portion 149. As a result, the support member 145 is attached to the outer peripheral portion of the probe 113.

Other characteristic technical matters according to the present invention are additionally set forth below.

Notes (Additional Note 1)

A medical treatment device comprising:

a fixed handle which includes a fixed side finger placing portion, and which extends along a longitudinal axis;

a movable handle which includes a movable side finger placing portion, the movable handle being configured to open/close relative to the fixed handle in a first open/close direction perpendicular to the longitudinal axis and in a second open/close direction opposite to the first open/close direction, and the movable handle being located to the first open/close direction side of the fixed handle;

an inclined plane which is provided in a part located to a distal direction side of the fixed side finger placing portion and in a part of the fixed handle located on the second open/close direction side, the inclined plane being inclined relative to the longitudinal axis, and in the inclined plane it going toward a proximal direction side as it goes from the first open/close direction toward the second open/close direction; and an operation input section provided in the inclined plane, the press direction of the operation input section being perpendicular to the inclined plane.

(Additional Note 2)

The medical treatment device according to Additional note 1, wherein the operation input section includes a first operation input section and a second operation input section, and the inclined plane includes a first inclined plane perpendicular to the press direction of the first operation input section, and a second inclined plane perpendicular to the press direction of the second operation input section, the first operation input section being provided in the first inclined plane, the second operation input section being provided in the second inclined plane, and the second inclined plane being located to the proximal direction side of the first inclined plane.

(Additional Note 3)

The medical treatment device according to Additional note 2, wherein an acute first angle between the first inclined plane and the longitudinal axis is greater than an acute second angle between the second inclined plane and the longitudinal axis.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment device comprising:
a probe extending along a longitudinal axis;
a sheath through which the probe is inserted so that the probe protrudes toward a distal direction;
a jaw which is attached to a distal portion of the sheath rotatably around a rotation axis perpendicular to the longitudinal axis, and which is configured to open/close relative to a distal portion of the probe in open/close directions perpendicular to the longitudinal axis and perpendicular to the rotation axis;
a fixing member which is provided between the probe and the sheath, and which is configured to fix a most-distal fixed position of the probe with respect to the sheath in a state that the fixing member prevents contact between the probe and the sheath, the most-distal fixed position of the probe being at a position where the probe is fixed with respect to the sheath on the most distal direction side in directions parallel to the longitudinal axis; and
an attachment portion which attaches the jaw to the sheath in a state that the rotation axis of the jaw passes through the probe at the most-distal fixed position.

2. The grasping treatment device according to claim 1, wherein the distal portion of the probe includes a jaw facing portion which faces the jaw, the jaw includes a probe facing portion which faces the distal portion of the probe, and the probe facing portion is separate from the jaw facing portion at a predetermined distance when the probe facing portion of the jaw is parallel to the jaw facing portion of the probe.

3. The grasping treatment device according to claim 1, wherein
the probe is configured to transmit ultrasonic vibrations from a proximal end to a distal end along the longitudinal axis, and
in the directions parallel to the longitudinal axis, the position of the rotation axis of the jaw and the position of the fixing member coincide with a node position of ultrasonic waves.

4. The grasping treatment device according to claim 1, wherein the probe includes a first electrode portion provided in the distal portion thereof, and is configured to transmit a high-frequency current along the longitudinal axis, the sheath is provided to an outer peripheral direction side of the probe in a state that the sheath is insulated from the probe, and the probe is inserted through the sheath in a state that the first electrode portion protrudes toward the distal direction, and the jaw includes a second electrode portion electrically connected to the sheath, and is configured to open/close relative to the first electrode portion in the open/close directions.

5. The grasping treatment device according to claim 4, further comprising an electric contact unit, the electric contact unit including a sheath side contact portion provided in an outer peripheral portion of the sheath, and a jaw side contact portion which is provided in an inner peripheral portion of the jaw, and which slidably contacts the sheath side contact portion, the electric contact unit being configured to maintain constant contact between the jaw side contact portion and the sheath side contact portion, and thereby configured to maintain constant transmission of the high-frequency current between the sheath and the second electrode portion of the jaw, wherein the electric contact unit includes a groove defining portion which defines a groove provided in the jaw to be recessed toward an outer peripheral direction along the rotation axis, the groove defining portion including a groove bottom surface where the jaw side contact portion is located, and a projection which is provided in the outer peripheral portion of the sheath to protrude toward the outer peripheral direction along the rotation axis, and which is inserted into the groove, the projection including a protruding end where the sheath side contact portion is located, or a groove defining portion which defines a groove provided in the outer peripheral portion of the sheath to be recessed toward an inner peripheral direction along the rotation axis, the groove defining portion including a groove bottom surface where the sheath side contact portion is located, and a projection which is provided in the jaw to protrude toward the inner peripheral direction along the rotation axis, and which is inserted into the groove, the projection including a protruding end where the jaw side contact portion is located, and the electric contact unit is configured such that (i) the projection includes a projection side sectional changing portion which is configured to decrease in the sectional area perpendicular to the rotation axis as it goes toward the protruding end along the rotation axis, and which is configured to reduce the area of contact between the sheath side contact portion and the jaw side contact portion, and/or (ii) the groove defining portion includes a convex portion which defines the groove bottom surface so that the sheath side contact portion or the jaw side contact portion protrudes toward the protruding end of the protrusion, and the convex portion includes a groove side sectional changing portion which is configured to decrease in the sectional area perpendicular to the rotation axis as it goes toward the sheath side contact portion or the jaw side contact portion along the rotation axis, and which is configured to reduce the area of contact between the sheath side contact portion and the jaw side contact portion.

6. The grasping treatment device according to claim 5, wherein a first dimension along the rotation axis from the longitudinal axis to the sheath side contact portion is greater than a second dimension along the rotation axis from the longitudinal axis to the jaw side contact portion when the jaw is not attached to the sheath.

7. The grasping treatment device according to claim 5, wherein the groove defining portion includes a first groove defining portion which defines a first groove recessed toward a first rotation axis direction parallel to the rotation axis, and a second groove defining portion which defines a second groove recessed toward a second rotation axis direction opposite to the first rotation axis direction, and the projection includes a first projection which protrudes toward the first rotation axis direction, and which is inserted in the first groove, and a second projection which protrudes toward the second rotation axis direction, and which is inserted in the second groove.

8. The grasping treatment device according to claim 5, wherein the projection side sectional changing portion is a projection side semispherical portion semispherically provided to extend to the sheath side contact portion or the jaw side contact portion along the rotation axis.

9. The grasping treatment device according to claim 5, wherein the groove side sectional changing portion is a groove side semispherical portion semispherically provided to extend to the sheath side contact portion or the jaw side contact portion along the rotation axis.

10. The grasping treatment device according to claim 1, further comprising:
a support member which is provided between the probe and the sheath, and which is configured to prevent contact between the probe and the sheath,
wherein the fixing member is a most-distal support member which is located on the most distal direction side among the support member.

* * * * *